US012753263B2

(12) United States Patent
Qu et al.

(10) Patent No.: US 12,753,263 B2
(45) Date of Patent: Oct. 6, 2026

(54) POLYMER AND COMPOSITION THEREOF

(71) Applicants: SHANGHAI SENHUI MEDICINE CO., LTD., Shanghai (CN); JIANGSU HENGRUI PHARMACEUTICALS CO., LTD., Lianyungang (CN)

(72) Inventors: Ximing Qu, Shanghai (CN); Fan Wu, Shanghai (CN); Lei Feng, Shanghai (CN); Peng Huang, Shanghai (CN); Jian Huang, Shanghai (CN)

(73) Assignees: SHANGHAI SENHUI MEDICINE CO., LTD., Shanghai (CN); JIANGSU HENGRUI PHARMACEUTICALS CO., LTD., Lianyungang (CN)

( * ) Notice: Subject to any disclaimer, the term of this patent is extended or adjusted under 35 U.S.C. 154(b) by 256 days.

(21) Appl. No.: 18/288,970

(22) PCT Filed: Apr. 29, 2022

(86) PCT No.: PCT/CN2022/090327

§ 371 (c)(1),
(2) Date: Oct. 30, 2023

(87) PCT Pub. No.: WO2022/228555

PCT Pub. Date: Nov. 3, 2022

(65) Prior Publication Data

US 2024/0228688 A1 Jul. 11, 2024

(30) Foreign Application Priority Data

Apr. 30, 2021 (CN) ......................... 202110479406.2
Oct. 12, 2021 (CN) ......................... 202111188454.2

(51) Int. Cl.
*C08F 293/00* (2006.01)
*A61K 9/00* (2006.01)
*A61K 9/06* (2006.01)

(52) U.S. Cl.
CPC .......... *C08F 293/00* (2013.01); *A61K 9/0019* (2013.01); *A61K 9/06* (2013.01)

(58) Field of Classification Search
CPC .................................................... C08J 2300/14
See application file for complete search history.

(56) References Cited

FOREIGN PATENT DOCUMENTS

| | | | |
|---|---|---|---|
| CN | 101845120 A | | 9/2010 |
| CN | 102477155 | * | 5/2012 |
| CN | 107929231 A | | 4/2018 |
| EP | 1988108 A1 | | 11/2008 |
| WO | WO2020225538 | * | 12/2020 |

OTHER PUBLICATIONS

Lee et al. (Sol-gel transition behavior of biodegradable three-arm and four-arm star-shaped PLGA-PEG block copolymer aqueous solution. J. Polym. Sci. A Polym. Chem., 44: 888-899, 2006). (Year: 2006).*

Movassaghian et al. (WIREs Nanomed Nanobiotechnol 2015, 7:691-707). (Year: 2015).*

Bozhen, CN 102477155, published: May 30, 2012, English machine translation obtained Jan. 22, 2026. (Year: 2026).*

Byeongmoon Jeong et al., Biodegradable block copolymers as injectable drug-delivery systems, Aug. 28, 1997, Nature, vol. 388, No. 6645, pp. 860-862 (3 pages). doi: 10.1038/42218.

Dhawal D. Ankola et al., Multiblock Copolymers of Lactic Acid and Ethylene Glycol Containing Periodic Side-Chain Carboxyl Groups: Synthesis, Characterization, and Nanoparticle Preparation, Macromolecules, 2009, vol. 42, No. 19, pp. 7388-7395 (8 pages). doi:10.1021/ma9012253.

Raghu Ganugula et al., Next Generation Precision-Polyesters Enabling Optimization of Ligand-Receptor Stoichiometry for Modular Drug Delivery, Journal of the American Chemical Society, May 31, 2017, vol. 139, No. 21 , pp. 7203-7216 (14 pages). doi: 10.1021/jacs.6b13231. Epub Apr. 19, 2017. PMID: 28395139.

* cited by examiner

*Primary Examiner* — Genevieve S Alley
(74) *Attorney, Agent, or Firm* — Morgan, Lewis & Bockius LLP

(57) ABSTRACT

The present application relates to a polymer and a composition thereof, and specifically provides a thermosensitive polymer represented by formula (I-2) and a preparation method therefor, and a pharmaceutical composition containing same, the polymer having a star-shaped multi-arm structure, and comprising an aromatic core and a biodegradable AB-type amphiphilic copolymer. The polymer can enhance the solubility and stability of a drug or a bioactive agent and control the release of the drug or the bioactive agent. The definition of each group in formula (I-2) is the same as in the description.

(I-2)

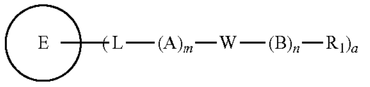

21 Claims, 10 Drawing Sheets

POLYMER AND COMPOSITION THEREOF

CROSS-REFERENCE TO RELATED APPLICATIONS

The present application is a national stage application of International Patent Application No. PCT/CN2022/090327, filed Apr. 29, 2022, which claims priority to Chinese Patent Application CN202110479406.2 filed on Apr. 30, 2021 and Chinese Patent Application CN202111188454.2 filed on Oct. 12, 2021, which are incorporated herein by reference in their entirety.

TECHNICAL FIELD

The present disclosure belongs to the field of pharmaceutics and relates to a thermosensitive polymer, a preparation method therefor and pharmaceutical use thereof. Particularly, the present disclosure relates to a thermosensitive star-shaped polymer for use in the preparation of a hydrogel long-acting sustained-release formulation.

BACKGROUND

Hydrogels are polymer network systems with a hydrophilic three-dimensional network structure. They are soft and maintain specific shapes. They have good biocompatibility and are widely applied to various aspects, such as tissue engineering, drug delivery, 3D cell culture, and other medical fields.

Among hydrogels, there are thermosensitive hydrogel materials that are particularly important in fields such as biomedicine. At around human body temperature, they are gels, but when the temperature deviates from human body temperature, they become solutions. Such thermosensitive hydrogels in a solution state can be used to embed bioactive substances such as polypeptides, proteins and cells. Upon injection into subcutaneous tissue or muscle tissue, the solution in which an active substance is embedded transitions into a gel quickly due to temperature change. The active substance is stably released from inside the gel by the combined action of diffusion and the self-degradation of the gel, so that a long-acting sustained-release effect is achieved. As no organic solvent is involved in the embedding process, the embedded active substance will not be easily inactivated, which is a significant advantage. Moreover, the injection implantation of thermosensitive hydrogels is non-surgical and minimally invasive and thus is easier and simpler than the implantation and embedding of other solid formulations.

Polymers with thermosensitive gelation properties are generally amphiphilic. Amphiphilic block copolymers include linear copolymers, star-shaped copolymers, graft copolymers and dendritic copolymers. However, studies on amphiphilic block copolymers for hydrogel preparation focus primarily on linear block copolymers. MacroMed Inc. developed a linear injectable thermosensitive hydrogel PLGA-PEG-PLGA (1500-1000-1500) under the trade name ReGel for use as a drug carrier. For the first time, Jeong et al. reported a triblock copolymer mPEG-PLGA-mPEG. The aqueous polymer solution flows freely at room temperature and forms a gel when the temperature is increased to body temperature. The solution forms a gel in situ upon injection into the back of a mouse (see "Biodegradable block copolymers as injectable drug-delivery systems.", Nature. 1997 Aug. 28:388(6645):860-2. doi: 10.1038/42218).

SUMMARY

The present disclosure provides a thermosensitive polymer or compound, which has a star-shaped multi-arm structure and comprises an aromatic core and a biodegradable AB-type amphiphilic copolymer, the biodegradable AB-type amphiphilic copolymer comprising a hydrophobic block A and a hydrophilic block B.

In some embodiments, the hydrophilic block B makes up about 10-about 90 wt % of the biodegradable AB-type amphiphilic copolymer. In some embodiments, the hydrophilic block B makes up about 20-about 80 wt %, about 20-about 60 wt %, about 25-about 50 wt % or about 30-about 40 wt % of the biodegradable AB-type amphiphilic copolymer.

In some specific embodiments, the hydrophilic block B makes up about 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt % or 90 wt % of the biodegradable AB-type amphiphilic copolymer.

In some embodiments, the hydrophobic block A makes up about 90-about 10 wt % of the biodegradable AB-type amphiphilic copolymer. In some embodiments, the hydrophobic block A makes up about 80-about 20 wt %, about 80-about 40 wt %, about 75-about 50 wt %, or about 70-about 60 wt % of the biodegradable AB-type amphiphilic copolymer.

In some specific embodiments, the hydrophobic block A makes up about 90 wt %, 89 wt %, 88 wt %, 87 wt %, 86 wt %, 85 wt %, 84 wt %, 83 wt %, 82 wt %, 81 wt %, 80 wt %, 79 wt %, 78 wt %, 77 wt %, 76 wt %, 75 wt %, 74 wt %, 73 wt %, 72 wt %, 71 wt %, 70 wt %, 69 wt %, 68 wt %, 67 wt %, 66 wt %, 65 wt %, 64 wt %, 63 wt %, 62 wt %, 61 wt %, 60 wt %, 59 wt %, 58 wt %, 57 wt %, 56 wt %, 55 wt %, 54 wt %, 53 wt %, 52 wt %, 51 wt %, 50 wt %, 49 wt %, 48 wt %, 47 wt %, 46 wt %, 45 wt %, 44 wt %, 43 wt %, 42 wt %, 41 wt %, 40 wt %, 39 wt %, 38 wt %, 37 wt %, 36 wt %, 35 wt %, 34 wt %, 33 wt %, 32 wt %, 31 wt %, 30 wt %, 29 wt %, 28 wt %, 27 wt %, 26 wt %, 25 wt %, 24 wt %, 23 wt %, 22 wt %, 21 wt %, 20 wt %, 19 wt %, 18 wt %, 17 wt %, 16 wt %, 15 wt %, 14 wt %, 13 wt %, 12 wt %, 11 wt % or 10 wt % of the biodegradable AB-type amphiphilic copolymer.

In some embodiments, a solution of the thermosensitive polymer or compound undergoes a solution-gel phase transition as the temperature increases, and the temperature of the solution-gel phase transition is about 4° C.-about 40° C.: in some embodiments, the temperature of the solution-gel phase transition is about 10° C.-about 37° C., or about 20° C.-about 37° C.

In some specific embodiments, the temperature of the solution-gel phase transition is about 4° ° C., 5° ° C., 6° C., 7° C., 8° C., 9° C., 10° C., 11° C., 12° C., 13° C., 14° C., 15° C., 16° C., 17° C., 18° C., 19° C., 20° C., 21° ° C., 22° C., 23° C., 24° C., 25° C., 26° C., 27° C., 28° C., 29° C., 30° C., 31° C., 32° ° C., 33° C., 34° C., 35° C., 36° ° C., 37° C., 38° C., 39° C. or 40° C.

In some embodiments, the hydrophilic block B is selected from the group consisting of polyethylene glycol and polyvinylpyrrolidone. In some embodiments, the hydrophilic block B is selected from polyethylene glycol. In some embodiments, the hydrophilic block B is selected from polyethylene glycol in the form of a monomethyl ether or monoethyl ether.

In some embodiments, the hydrophilic block B has a weight-average molecular weight of about 100-about 20,000. In some embodiments, the hydrophilic block B has a weight-average molecular weight of about 200-about 5300. In some embodiments, the hydrophilic block B has a weight-average molecular weight of about 400-about 1000.

In some specific embodiments, the hydrophilic block B has a weight-average molecular weight of about 200, 300, 400, 410, 420, 430, 440, 450, 460, 470, 480, 490, 500, 510, 520, 530, 540, 550, 560, 570, 580, 590, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000 or 20,000.

In some embodiments, the hydrophilic block B has a number-average molecular weight that is less than the weight-average molecular weight.

In some embodiments, the hydrophilic block B has a number-average molecular weight of about 100-about 20,000. In some embodiments, the hydrophilic block B has a number-average molecular weight of about 200-about 5300. In some embodiments, the hydrophilic block B has a number-average molecular weight of about 400-about 1000.

In some specific embodiments, the hydrophilic block B has a number-average molecular weight of about 200, 300, 400, 410, 420, 430, 440, 450, 460, 470, 480, 490, 500, 510, 520, 530, 540, 550, 560, 570, 580, 590, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000 or 20,000.

In the present disclosure, the number-average molecular weight (Mn) and weight-average molecular weight (Mw) of the hydrophilic block B are determined by gel permeation chromatography (GPC, polyethylene glycol as standard).

In some embodiments, the hydrophobic block A is selected from the group consisting of a polyester and a polyamino acid. In some embodiments, the hydrophobic block A is selected from one of poly(DL-lactic acid), poly (D-lactic acid), poly(L-lactic acid), poly(DL-lactic acid-glycolic acid), poly(L-lactic acid-glycolic acid), poly(D-lactic acid-glycolic acid), poly-caprolactone, poly(DL-lactic acid-caprolactone), poly(L-lactic acid-caprolactone), poly (D-lactic acid-caprolactone), polyglycine, polyalanine, polyphenylalanine, polyglutamic acid, polylysine, polyornithine and polyarginine or a copolymer thereof.

In some embodiments, the hydrophobic block A has a weight-average molecular weight of about 72-about 60,000. In some embodiments, the hydrophobic block A has a weight-average molecular weight of about 150-about 20,000. In some embodiments, the hydrophobic block A has a weight-average molecular weight of about 200-about 15,000. In some embodiments, the hydrophobic block A has a weight-average molecular weight of about 300-about 10,000. In some embodiments, the hydrophobic block A has a weight-average molecular weight of about 400-about 8000. In some embodiments, the hydrophobic block A has a weight-average molecular weight of about 500-about 3000. In some embodiments, the hydrophobic block A has a weight-average molecular weight of about 700-about 2000.

In some specific embodiments, the hydrophobic block A has a weight-average molecular weight of about 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000, 20,000, 30,000, 40,000, 50,000 or 60,000.

In some embodiments, the hydrophobic block A has a number-average molecular weight that is less than the weight-average molecular weight.

In some embodiments, the hydrophobic block A has a number-average molecular weight of about 72-about 60,000. In some embodiments, the hydrophobic block A has a number-average molecular weight of about 150-about 20,000. In some embodiments, the hydrophobic block A has a number-average molecular weight of about 200-about 15,000. In some embodiments, the hydrophobic block A has a number-average molecular weight of about 300-about 10,000. In some embodiments, the hydrophobic block A has a number-average molecular weight of about 400-about 8000. In some embodiments, the hydrophobic block A has a number-average molecular weight of about 500-about 3000. In some embodiments, the hydrophobic block A has a number-average molecular weight of about 700-about 2000.

In some specific embodiments, the hydrophobic block A has a number-average molecular weight of about 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000, 20,000, 30,000, 40,000, 50,000 or 60,000.

In the present disclosure, the number-average molecular weight (Mn) and weight-average molecular weight (Mw) of the hydrophobic block A are determined by gel permeation chromatography (GPC, polyethylene glycol as standard).

In some embodiments, the thermosensitive polymer or compound of the present disclosure has a weight-average molecular weight of about 200-about 300,000. In some embodiments, the thermosensitive polymer or compound has a weight-average molecular weight of about 500-about 100,000. In some embodiments, the thermosensitive polymer or compound has a weight-average molecular weight of about 1000-about 50,000. In some embodiments, the thermosensitive polymer or compound has a weight-average molecular weight of about 2000-about 10,000. In some embodiments, the thermosensitive polymer or compound has a weight-average molecular weight of about 1000-about 8000.

In some specific embodiments, the thermosensitive polymer or compound of the present disclosure has a weight-average molecular weight of about 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000 or 300,000.

In some embodiments, the thermosensitive polymer or compound of the present disclosure has a number-average molecular weight that is less than the weight-average molecular weight.

In some embodiments, the thermosensitive polymer or compound of the present disclosure has a number-average molecular weight of about 200-about 300,000. In some embodiments, the thermosensitive polymer or compound has a number-average molecular weight of about 500-about 100,000. In some embodiments, the thermosensitive polymer or compound has a number-average molecular weight of about 1000-about 50,000. In some embodiments, the thermosensitive polymer or compound has a number-average molecular weight of about 2000-about 10,000. In some embodiments, the thermosensitive polymer or compound has a number-average molecular weight of about 800-about 7000.

In some specific embodiments, the thermosensitive polymer or compound of the present disclosure has a number-average molecular weight of about 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000 or 300,000.

In the present disclosure, the number-average molecular weight (Mn) and weight-average molecular weight (Mw) of the thermosensitive polymer or compound are determined by gel permeation chromatography (GPC, polyethylene glycol as standard).

The thermosensitive polymer or compound of the present disclosure has a molecular weight distribution coefficient (Mw/Mn) of less than 2.

In some embodiments, the thermosensitive polymer or compound of the present disclosure has a molecular weight distribution coefficient (Mw/Mn) of less than 2. In some embodiments, the molecular weight distribution coefficient is less than 1.5. In some embodiments, the molecular weight distribution coefficient is less than 1.4. In some embodiments, the molecular weight distribution coefficient is less than 1.3. In some embodiments, the molecular weight distribution coefficient is less than 1.2. In some embodiments, the molecular weight distribution coefficient is less than 1.18. In some embodiments, the molecular weight distribution coefficient is less than 1.15.

In some specific embodiments, the molecular weight distribution coefficient of the thermosensitive polymer or compound of the present disclosure is selected from the group consisting of about 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99 and 2.00.

In some embodiments, the thermosensitive polymer or compound has a structure of formula (I), (I)

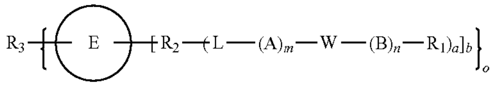

wherein $R_1$ are identical or different and are each independently selected from $C_1$-$C_{12}$ alkyl (e.g., $C_1$, $C_2$, $C_3$, $C_4$, $C_5$, $C_6$, $C_7$, $C_8$, $C_9$, $C_{10}$, $C_{11}$ or $C_{12}$), and the $C_1$-$C_{12}$ alkyl is optionally substituted with one or more substituents selected from the group consisting of halogen, hydroxy, alkoxy, haloalkoxy, cyano, amino and nitro;

$R_2$ and $R_3$ are identical or different and are each independently selected from the group consisting of absent, —O—, —S—, —SO—, —$SO_2$—, —C(O)—, —C(O)O—, —NR'—, —C(O)NR'—, alkylene, alkenylene, alkynylene, heteroalkylene, cycloalkylene, heterocycloalkylene, arylene, heteroarylene, PEG, an alkyl group of 1-20 (e.g., 1, 2, 3, 4, 5, 6, 7, 8, 9, 10, 11, 12, 13, 14, 15, 16, 17, 18, 19 or 20) carbon atoms which may have a branched structure, and an alkoxy group of 1-20 (e.g., 1, 2, 3, 4, 5, 6, 7, 8, 9, 10, 11, 12, 13, 14, 15, 16, 17, 18, 19 or 20) carbon atoms which may have a branched structure; the alkylene, alkenylene, alkynylene, heteroalkylene, cycloalkylene, heterocycloalkylene, arylene, heteroarylene, alkyl or alkoxy is optionally substituted with one or more substituents selected from the group consisting of hydroxy, alkyl, alkoxy, haloalkyl, haloalkoxy, halogen, cyano, amino and nitro; the R' is selected from the group consisting of hydrogen, deuterium, hydroxy, alkyl, alkoxy, cycloalkyl, heterocyclyl, aryl and heteroaryl, and the alkyl, alkoxy, cycloalkyl, heterocyclyl, aryl or heteroaryl is optionally substituted with one or more substituents selected from the group consisting of halogen, hydroxy, oxo, nitro and cyano;

rings E are identical or different and are each independently selected from the group consisting of aryl and heteroaryl: in some embodiments, rings E are identical or different and are each independently selected from the group consisting of $C_6$-$C_{12}$ (e.g., $C_6$, $C_7$, $C_8$, $C_9$, $C_{10}$, $C_{11}$ or $C_{12}$) aryl and 5-10 membered (e.g., 5-membered, 6-membered, 7-membered, 8-membered, 9-membered or 10-membered) heteroaryl: in some embodiments, rings E are identical or different and are each independently selected from the group consisting of phenyl, pyridinyl, pyrazinyl, pyrazolyl, triazolyl, isoxazolyl, oxazolyl, thiazolyl, thiadiazolyl, imidazolyl, indazolyl and benzimidazolyl;

L are identical or different and are each independently selected from the group consisting of a bond, —C(O)—, —O—, —S—, —SO—, —$SO_2$—, —C(O)O—, —NR'—, —C(O)NR'—, alkylene, alkenylene, alkynylene, heteroalkylene, cycloalkylene, heterocycloalkylene, arylene, heteroarylene and PEG, and the alkylene, alkenylene, alkynylene, heteroalkylene, cycloalkylene, heterocycloalkylene, arylene or heteroarylene is optionally substituted with one or more substituents selected from the group consisting of hydroxy, alkyl, alkoxy, haloalkyl, haloalkoxy, halogen, cyano, amino and nitro: the R' is selected from the group consisting of hydrogen, deuterium, hydroxy, alkyl, alkoxy, cycloalkyl, heterocyclyl, aryl and heteroaryl, and the alkyl, alkoxy, cycloalkyl, heterocyclyl, aryl or heteroaryl is optionally substituted with one or more more substituents selected from the group consisting of halogen, hydroxy, oxo, nitro and cyano;

A is selected from a hydrophobic block;

in some embodiments, the hydrophobic block is selected from the group consisting of a polyester and a polyamino acid: in some embodiments, the hydrophobic block is selected from one of poly(DL-lactic acid), poly(D-lactic acid), poly(L-lactic acid), poly(DL-lactic acid-glycolic acid), poly(L-lactic acid-glycolic acid), poly(D-lactic acid-glycolic acid), poly-caprolactone, poly(DL-lactic acid-caprolactone), poly(L-lactic acid-caprolactone), poly(D-lactic acid-caprolactone), polyglycine, polyalanine, polyphenylalanine, polyglutamic acid, polylysine, polyornithine and polyarginine or a copolymer thereof;

B is selected from a hydrophilic block;

in some embodiments, the hydrophilic block is selected from the group consisting of polyethylene glycol and polyvinylpyrrolidone: in some embodiments, the hydrophilic block is selected from polyethylene glycol: in some embodiments, the hydrophilic block is selected from polyethylene glycol in the form of a monomethyl ether, monoethyl ether, dimethyl ether or glycerol ether;

W are identical or different and are each independently selected from the group consisting of a bond, —O—, —S—, —SO—, —$SO_2$—, —C(O)—, —C(O)O—, —NR'—, —C(O)NR'— and alkylene, and the alkylene is optionally substituted with one or more substituents selected from the group consisting of hydroxy, alkyl, alkoxy, haloalkyl, haloalkoxy, halogen, cyano, amino and nitro: the R' is selected from the group consisting of hydrogen, deuterium, hydroxy, alkyl, alkoxy, cycloalkyl, heterocyclyl, aryl and heteroaryl, and the alkyl, alkoxy, cycloalkyl, heterocyclyl, aryl or heteroaryl is optionally substituted with one or more substituents selected from the group consisting of halogen, hydroxy, oxo, nitro and cyano;

m is selected from an integer from 1-300; in some embodiments, m is selected from an integer from 5-150; in some embodiments, m is selected from an integer from 10-120; in some embodiments, m is selected from an integer from 10-45: in some embodiments, m is selected from an integer from 15-25;

in some specific embodiments, m is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 and 300;

n is selected from an integer from 1-500: in some embodiments, n is selected from an integer from 5-300; in some embodiments, n is selected from an integer from 10-45; in some embodiments, n is selected from an integer from 10-30: in some embodiments, n is selected from an integer from 10-20;

in some specific embodiments, n is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 and 500;

a is selected from an integer from 1-20; in some embodiments, a is selected from an integer from 2-15: in some embodiments, a is selected from an integer from 3-11: in some embodiments, a is selected from an integer from 4-8;

in some specific embodiments, a is selected from the group consisting of 1, 2, 3, 4, 5, 6, 7, 8, 9, 10, 11, 12, 13, 14, 15, 16, 17, 18, 19 and 20;

b is selected from the group consisting of 1, 2, 3, 4, 5 and 6;

is selected from the group consisting of 1, 2, 3 and 4.

In some embodiments, the structure of formula (I) is selected from the group consisting of:

(I-1)

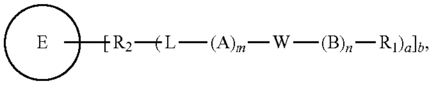

(I-2)

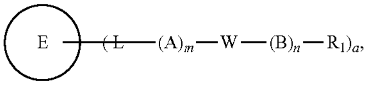

(I-3)

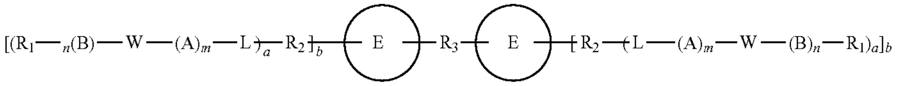

and (I-4)

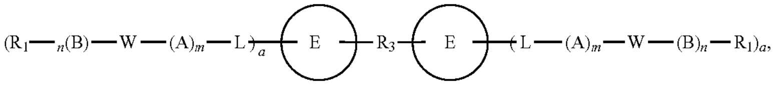

wherein $R_1$, $R_2$, $R_3$, ring E, L, A, B, W, m, n, a and b are as defined in formula (I).

In some embodiments, formula (I-1) is selected from (I-5)

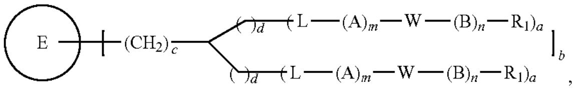

wherein c is selected from an integer from 1-8, such as 1, 2, 3, 4, 5, 6, 7 or 8;

d are identical or different and are each independently selected from an integer from 1-8, such as 1, 2, 3, 4, 5, 6, 7 or 8;

$R_1$, ring E, L, A, B, W, m, n, a and b are as defined in formula (I).

In some embodiments, formula (I-3) is selected from:

(I-6)

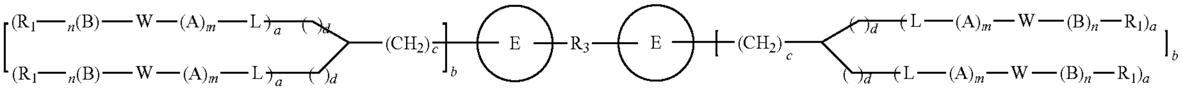

wherein c is selected from an integer from 1-8, such as 1, 2, 3, 4, 5, 6, 7 or 8;

d are identical or different and are each independently selected from an integer from 1-8, such as 1, 2, 3, 4, 5, 6, 7 or 8;

$R_1$, $R_3$, ring E, L, A, B, W, m, n, a and b are as defined in formula (I).

In some embodiments, ring E is selected from phenyl.

In some embodiments, formula (I) is selected from the group consisting of:

(II-1)

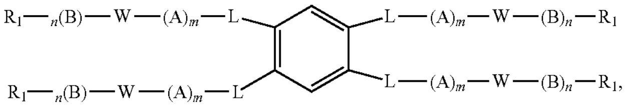

-continued (II-2)

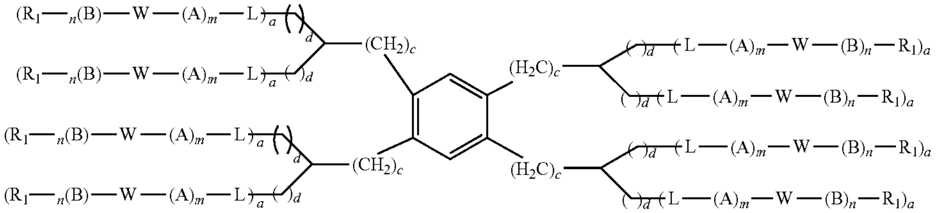

(II-3)

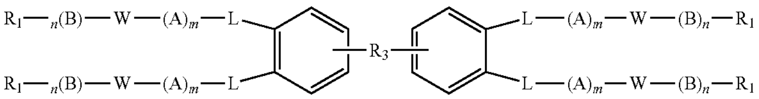

and (II-4)

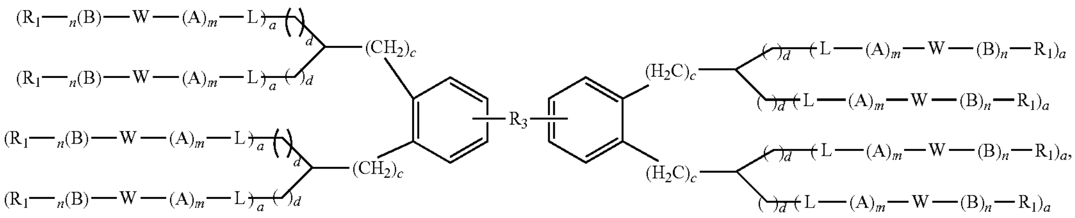

wherein:

c is selected from an integer from 1-8, such as 1, 2, 3, 4, 5, 6, 7 or 8;

d are identical or different and are each independently selected from an integer from 1-8, such as 1, 2, 3, 4, 5, 6, 7 or 8;

$R_1$, $R_2$, $R_3$, L, A, B, W, m, n and a are as defined in formula (I).

In formulas (II-1), (II-2), (II-3) and (II-4), L are identical or different and are each independently selected from the group consisting of a bond, —C(O)—, —O—, —S—, —SO—, —$SO_2$—, —C(O)O—, —NR'—, —C(O)NR'—, $C_1$-$C_6$ alkylene (e.g., $C_1$, $C_2$, $C_3$, $C_4$, $C_5$ or $C_6$) and PEG, and the alkylene is optionally substituted with one or more substituents selected from the group consisting of hydroxy, alkyl, alkoxy, haloalkyl, haloalkoxy, halogen, cyano, amino and nitro; the R' is selected from the group consisting of hydrogen, deuterium, hydroxy, $C_1$-$C_6$ alkyl (e.g., $C_1$, $C_2$, $C_3$, $C_4$, $C_5$ or $C_6$) and $C_1$-$C_6$ alkoxy (e.g., $C_1$, $C_2$, $C_3$, $C_4$, $C_5$ or $C_6$), and the $C_1$-$C_6$ alkyl (e.g., $C_1$, $C_2$, $C_3$, $C_4$, $C_5$ or $C_6$) or $C_1$-$C_6$ alkoxy (e.g., $C_1$, $C_2$, $C_3$, $C_4$, $C_5$ or $C_6$) is optionally substituted with one or more substituents selected from the group consisting of halogen, hydroxy, oxo, nitro and cyano: in some embodiments, L is selected from the group consisting of —O—, —C(O)—, —C(O)NH— and —C(O)O—.

In formulas (II-1), (II-2), (II-3) and (II-4), W are identical or different and are each independently selected from the group consisting of a bond, —O—, —C(O)— and —NH—.

In formulas (II-1), (II-2), (II-3) and (II-4), $R_1$ are identical or different and are each independently selected from $C_1$-$C_6$ alkyl (e.g., $C_1$, $C_2$, $C_3$, $C_4$, $C_5$ or $C_6$), and the $C_1$-$C_6$ alkyl is optionally substituted with one or more substituents selected from the group consisting of halogen, hydroxy, alkoxy, haloalkoxy, cyano, amino and nitro; and is preferably selected from the group consisting of methyl, ethyl, n-propyl, isopropyl, n-butyl, isobutyl and tert-butyl, optionally substituted with one or more substituents selected from the group consisting of hydroxy, alkyl, alkoxy, haloalkyl, haloalkoxy, halogen, hydroxy, cyano, amino and nitro.

In formulas (II-1), (II-2), (II-3) and (II-4), $R_3$ is selected from the group consisting of a bond, —O—, —S—, —SO—, —$SO_2$—, —C(O)—, —C(O)O—, —NR'—, —C(O)NR'—, $C_1$-$C_6$ alkylene (e.g., $C_1$, $C_2$, $C_3$, $C_4$, $C_5$ or $C_6$) and PEG, and the $C_1$-$C_6$ alkylene is optionally substituted with one or more substituents selected from the group consisting of hydroxy, alkyl, alkoxy, haloalkyl, haloalkoxy, halogen, cyano, amino and nitro: the R' is selected from the group consisting of hydrogen, deuterium, hydroxy, $C_1$-$C_6$ alkyl (e.g., $C_1$, $C_2$, $C_3$, $C_4$, $C_5$ or $C_6$) and $C_1$-$C_6$ alkoxy (e.g., $C_1$, $C_2$, $C_3$, $C_4$, $C_5$ or $C_6$), and the $C_1$-$C_6$ alkyl or $C_1$-$C_6$ alkoxy is optionally substituted with one or more substituents selected from the group consisting of halogen, hydroxy, oxo, nitro and cyano: in some embodiments, from the group consisting of a bond, —O—, —S—, —C(O)— and —$SO_2$—.

In formulas (II-1), (II-2), (II-3) and (II-4), a are identical or different and are each independently selected from the group consisting of 1, 2, 3, 4, 5 and 6.

In formulas (II-1), (II-2), (II-3) and (II-4), c are identical or different and are each independently selected from the group consisting of 1, 2, 3 and 4.

In formulas (II-1), (II-2), (II-3) and (II-4), d are identical or different and are each independently selected from the group consisting of 1, 2, 3 and 4.

In formulas (II-1), (II-2), (II-3) and (II-4), —$(B)_n$—$R_1$ is selected from —($CH_2CH_2O$) n-$R_1$, wherein $R_1$ is as defined above, and n is selected from an integer from 1-500; in some embodiments, n is selected from an integer from 10-300; in some embodiments, n is selected from an integer from 5-150; in some embodiments, n is selected from an integer from 10-120; in some embodiments, n is selected from an integer from 10-45: in some embodiments, n is selected from an integer from 10-20.

In some specific embodiments, n is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 and 500.

In formulas (II-1), (II-2), (II-3) and (II-4), $-(A)_m-$is selected from the group consisting of a polyester and a polyamino acid: in some embodiments, the $-(A)_m-$is selected from one of poly(DL-lactic acid), poly(D-lactic acid), poly (L-lactic acid), poly(DL-lactic acid-glycolic acid), poly(L-lactic acid-glycolic acid), poly(D-lactic acid-glycolic acid), poly-caprolactone, poly(DL-lactic acid-caprolactone), poly (L-lactic acid-caprolactone), poly(D-lactic acid-caprolactone), polyglycine, polyalanine, polyphenylalanine, polyglutamic acid, polylysine, polyornithine and polyarginine or a copolymer thereof.

In some embodiments, $W-(A)_m-L$ is selected from the group consisting of:

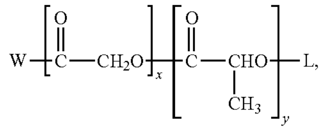

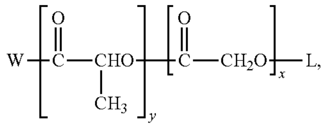

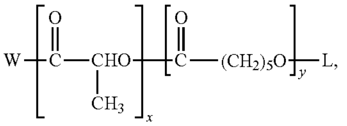

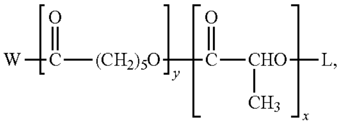

-continued

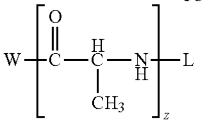

and

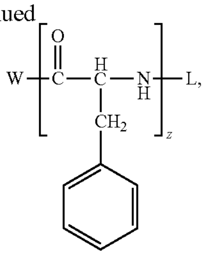

wherein

W and L are as defined above;

x is selected from an integer from 0-300; in some embodiments, x is selected from an integer from 0-50; in some embodiments, x is selected from an integer from 0-20; in some embodiments, x is selected from an integer from 3-10; in some embodiments, x is selected from an integer from 0-8;

in some specific embodiments, x is selected from the group consisting of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 and 300;

y is selected from 1-300; in some embodiments, y is selected from an integer from 5-70; in some embodiments, y is selected from an integer from 5-25; in some embodiments, y is selected from an integer from 5-20;

in some specific embodiments, y is selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 and 300;

z is selected from 10-300; in some embodiments, z is selected from an integer from 10-120; in some embodiments, z is selected from an integer from 10-45; in some embodiments, z is selected from an integer from 20-25;

in some specific embodiments, z is selected from the group consisting of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 and 300.

In some specific embodiments, the thermosensitive polymer or compound of the present disclosure is selected from:

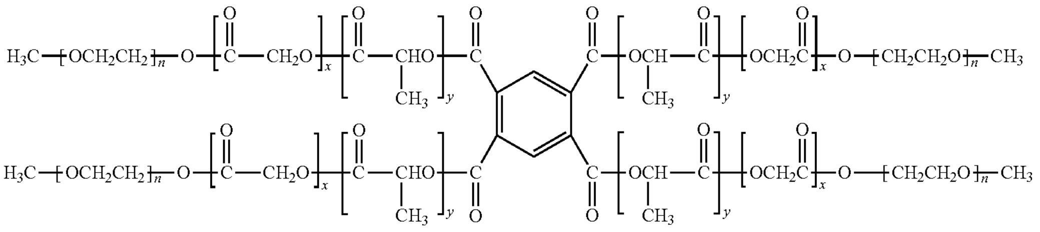

wherein n is selected from an integer from 5-15;

x is selected from an integer from 3-10;

y is selected from an integer from 5-20;

in some embodiments, n is selected from the group consisting of 5, 6, 7, 8, 9, 10, 11, 12, 13, 14 and 15;

in some embodiments, x is selected from the group consisting of 3, 4, 5, 6, 7, 8, 9 and 10;

in some embodiments, y is selected from the group consisting of 5, 6, 7, 8, 9, 10, 11, 12, 13, 14, 15, 16, 17, 18, 19 and 20.

In some specific embodiments, the thermosensitive polymer or compound of the present disclosure is selected from:

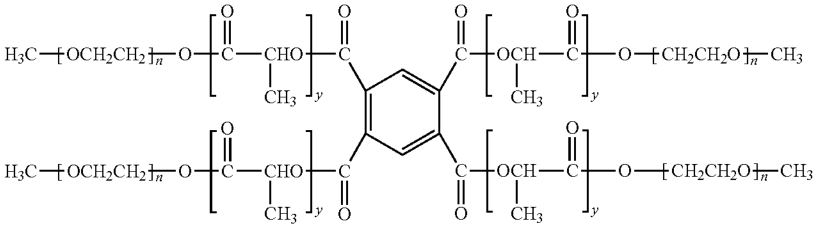

wherein n is selected from an integer from 5-15;

y is selected from an integer from 5-20;

in some embodiments, n is selected from the group consisting of 5, 6, 7, 8, 9, 10, 11, 12, 13, 14 and 15;

in some embodiments, y is selected from the group consisting of 5, 6, 7, 8, 9, 10, 11, 12, 13, 14, 15, 16, 17, 18, 19 and 20.

In some specific embodiments, the thermosensitive polymer or compound of the present disclosure is selected from:

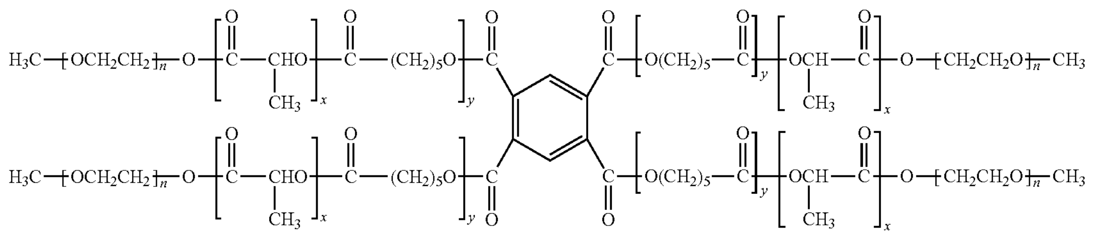

wherein n is selected from an integer from 5-15;

x is selected from an integer from 3-10;

y is selected from an integer from 5-20;

in some embodiments, n is selected from the group consisting of 5, 6, 7, 8, 9, 10, 11, 12, 13, 14 and 15;

in some embodiments, x is selected from the group consisting of 3, 4, 5, 6, 7, 8, 9 and 10;

in some embodiments, y is selected from the group consisting of 5, 6, 7, 8, 9, 10, 11, 12, 13, 14, 15, 16, 17, 18, 19 and 20.

In some specific embodiments, the thermosensitive polymer or compound of the present disclosure is selected from:

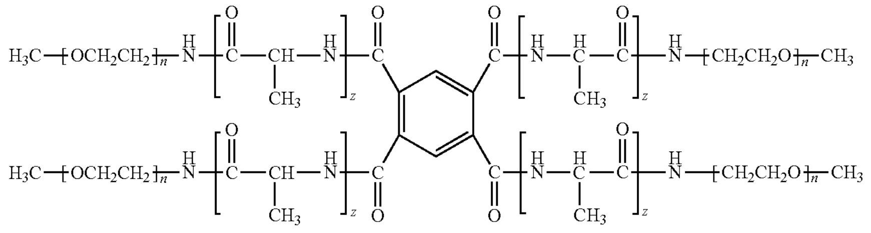

wherein n is selected from an integer from 5-15;

z is selected from an integer from 15-25;

in some embodiments, n is selected from the group consisting of 5, 6, 7, 8, 9, 10, 11, 12, 13, 14 and 15;

in some embodiments, z is selected from the group consisting of 15, 16, 17, 18, 19, 20, 21, 22, 23, 24 and 25.

In some specific embodiments, the thermosensitive polymer or compound of the present disclosure is selected from:

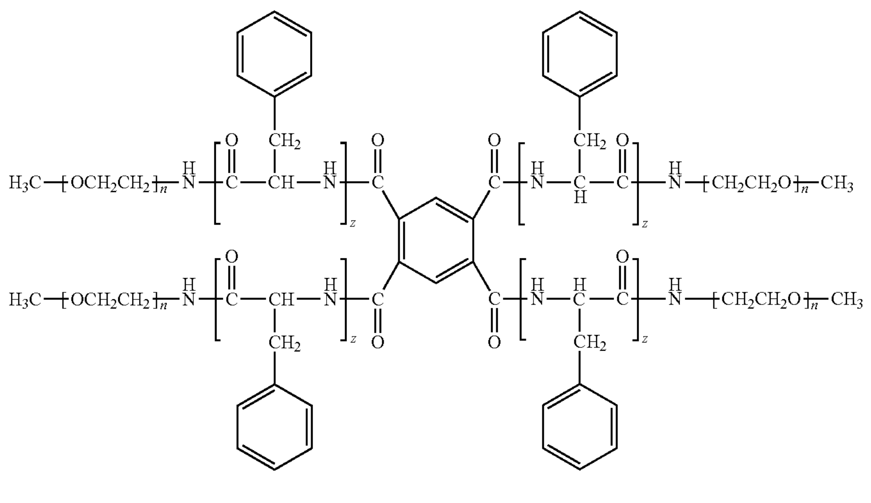

wherein n is selected from an integer from 5-15;

z is selected from an integer from 15-25;

in some embodiments, n is selected from the group consisting of 5, 6, 7, 8, 9, 10, 11, 12, 13, 14 and 15;

in some embodiments, z is selected from the group consisting of 15, 16, 17, 18, 19, 20, 21, 22, 23, 24 and 25.

In some specific embodiments, the thermosensitive polymer or compound of the present disclosure is selected from:

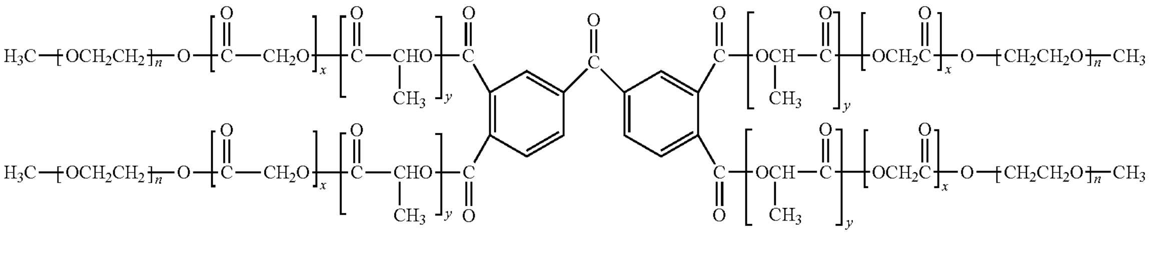

wherein n is selected from an integer from 5-15;

x is selected from an integer from 3-10;

y is selected from an integer from 5-20;

in some embodiments, n is selected from the group consisting of 5, 6, 7, 8, 9, 10, 11, 12, 13, 14 and 15;

in some embodiments, x is selected from the group consisting of 3, 4, 5, 6, 7, 8, 9 and 10;

in some embodiments, y is selected from the group consisting of 5, 6, 7, 8, 9, 10, 11, 12, 13, 14, 15, 16, 17, 18, 19 and 20.

In some specific embodiments, the thermosensitive polymer or compound of the present disclosure is selected from:

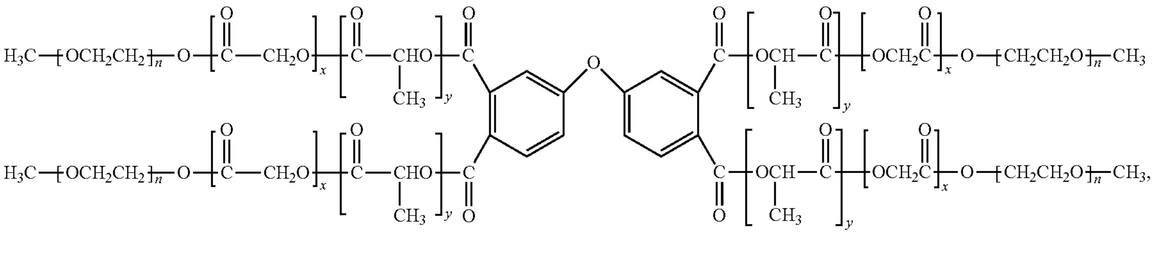

wherein n is selected from an integer from 5-15;

x is selected from an integer from 3-10;

y is selected from an integer from 5-20;

in some embodiments, n is selected from the group consisting of 5, 6, 7, 8, 9, 10, 11, 12, 13, 14 and 15;

in some embodiments, x is selected from the group consisting of 3, 4, 5, 6, 7, 8, 9 and 10;

in some embodiments, y is selected from the group consisting of 5, 6, 7, 8, 9, 10, 11, 12, 13, 14, 15, 16, 17, 18, 19 and 20.

The present disclosure further provides a method for preparing the thermosensitive polymer or compound comprising: chemically coupling an AB-type amphiphilic copolymer to an acid anhydride, acyl chloride, active ester or carboxylic acid comprising an aromatic ring or heteroaromatic ring by the action of a condensing agent or catalyst.

In some embodiments, the condensing agent is selected from one or more of dicyclohexylcarbodiimide, diisopropylcarbodiimide and 1-(3-dimethylaminopropyl)-3-ethylcarbodiimide.

In some embodiments, the catalyst is selected from one or more of 4-dimethylaminopyridine, 1-hydroxy benzotriazole and 4-pyrrolidinylpyridine.

In some embodiments, the AB-type amphiphilic copolymer is an amphiphilic copolymer comprising a hydrophobic block and a hydrophilic block.

In some embodiments, the hydrophilic block is selected from the group consisting of polyethylene glycol and polyvinylpyrrolidone, and the hydrophobic block is selected from the group consisting of a polyester and a polyamino acid.

In some embodiments, the hydrophobic block is selected from one of poly(DL-lactic acid), poly(D-lactic acid), poly (L-lactic acid), poly(DL-lactic acid-glycolic acid), poly(L-lactic acid-glycolic acid), poly(D-lactic acid-glycolic acid), poly-caprolactone, poly(DL-lactic acid-caprolactone), poly (L-lactic acid-caprolactone), poly(D-lactic acid-caprolactone), polyglycine, polyalanine, polyphenylalanine, polyglutamic acid, polylysine, polyornithine and polyarginine or a copolymer thereof.

In some embodiments, the hydrophilic block is selected from polyethylene glycol; in some embodiments, the hydrophilic block is selected from polyethylene glycol in the form of a monomethyl ether, monoethyl ether, dimethyl ether or glycerol ether: in some embodiments, the AB-type amphiphilic copolymer is mPEG-PLA or mPEG-PLGA.

The present disclosure further provides a composition or pharmaceutical composition comprising the thermosensitive polymer of the present disclosure or the compound of the present disclosure.

In some embodiments, the composition or pharmaceutical composition further comprises a vehicle: in some embodiments, the vehicle is selected from the group consisting of phosphate-buffered saline, purified water and normal saline.

In some embodiments, the concentration of the thermosensitive polymer or compound in the composition or pharmaceutical composition is 1-80 wt %; in some embodiments, the concentration is selected from the group consisting of 5-50 wt %, 10-70 wt %, 15-50 wt %, 20-40 wt % and 5-30 wt %.

In some specific embodiments, the concentration of the thermosensitive polymer or compound in the composition or pharmaceutical composition is about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt % or 80 wt %.

In some embodiments, the composition or pharmaceutical composition further comprises a drug or bioactive agent.

In some embodiments, the drug or bioactive agent includes, but is not limited to, nucleic acids, nucleotides, oligonucleotides, aptamers, siRNA, small-molecule drugs, sugars, polysaccharides, hormones, polypeptides, proteins, enzymes, cytokines, antibodies, vaccines, and combinations thereof. Examples include herceptin, interleukin-2, and the like.

In some embodiments, the drug or bioactive agent is an active ingredient for treating disease in humans or animals and may be selected from the group consisting of an antineoplastic agent, a cardiovascular agent, an anti-infective agent, an antifungal agent, an antiviral agent, an anti-allergic agent, an anti-inflammatory agent, an endocrine agent, a psychotropic agent, an antibiotic agent, an immunosuppressive agent, a vitamin, a narcotic, and the like. In some embodiments, the drug or bioactive agent in the composition is released in a sustained and/or controlled manner.

In some embodiments, the composition or pharmaceutical composition further comprises a pharmaceutically acceptable carrier and/or excipient.

In some embodiments, a unit dose of the composition or pharmaceutical composition is 0.001 mg-1000 mg.

In some embodiments, the composition comprises 0.01-99.99% of the drug or bioactive agent, or a pharmaceutically acceptable salt thereof, based on the total weight of the composition or pharmaceutical composition. In certain embodiments, the composition comprises 0.1-99.9% of the drug or bioactive agent, or a pharmaceutically acceptable salt thereof. In certain embodiments, the composition comprises 0.5%-99.5% of the drug or bioactive agent, or a pharmaceutically acceptable salt thereof. In certain embodiments, the composition comprises 1%-99% of the drug or bioactive agent, or a pharmaceutically acceptable salt thereof. In certain embodiments, the composition comprises 2%-98% of the drug or bioactive agent, or a pharmaceutically acceptable salt thereof.

In certain embodiments, the composition or pharmaceutical composition comprises 0.01%-99.99% of the pharmaceutically acceptable excipient, based on the total weight of the composition or pharmaceutical composition. In certain embodiments, the composition or pharmaceutical composition comprises 0.1%-99.9% of the pharmaceutically acceptable excipient. In certain embodiments, the composition or pharmaceutical composition comprises 0.5%-99.5% of the pharmaceutically acceptable excipient. In certain embodiments, the composition or pharmaceutical composition comprises 1%-99% of the pharmaceutically acceptable excipient. In certain embodiments, the composition or pharmaceutical composition comprises 2%-98% of the pharmaceutically acceptable excipient.

In some embodiments, the composition or pharmaceutical composition undergoes a solution-gel phase transition as the temperature increases, and the temperature of the solution-gel phase transition is 4-40° C.: in some embodiments, the temperature of the solution-gel phase transition is about 10-about 37° C., or about 20-about 37° C. In some embodiments, the temperature of the solution-gel phase transition is human body temperature.

In some specific embodiments, the temperature of the solution-gel phase transition of the composition or pharmaceutical composition is about 4° C., 5° C., 6° C., 7° C., 8° C., 9) ° C., 10° C., 11° C., 12° C., 13° C., 14° C., 15° C., 16° ° C., 17° C., 18° C., 19° C., 20° C., 21° ° C., 22° C., 23° C., 24° C., 25° ° C., 26° ° C., 27° ° C., 28° C., 29° C., 30° C., 31° C., 32° C., 33° C., 34° C., 35° C., 36° C., 37° C., 38° C., 39° C. or 40° C.

In some embodiments, the thermosensitive polymer or compound or the composition or pharmaceutical composition of the present disclosure is injectable.

The present disclosure further provides a hydrogel comprising the thermosensitive polymer of the present disclosure, or the compound of the present disclosure, or the composition or pharmaceutical composition of the present disclosure.

In some embodiments, the hydrogel undergoes a solution-gel phase transition as the temperature increases, and the temperature of the solution-gel phase transition is 4-40° C.; in some embodiments, the temperature of the solution-gel phase transition is about 10-about 37° C., or about 20-about 37° C. In some embodiments, the temperature of the solution-gel phase transition is human body temperature.

In some specific embodiments, the temperature of the solution-gel phase transition of the hydrogel is about 4° ° C., 5° C., 6° C., 7° C., 8° C., 9) ° C., 10° C., 11° C., 12° C., 13° C., 14° C., 15° C., 16° ° C., 17° C., 18° C., 19° C., 20° C., 21° ° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C.

The present disclosure provides a method for preparing a hydrogel comprising the following steps:

(1) chemically coupling the AB-type amphiphilic copolymer of the present disclosure to an acid anhydride, acyl chloride, active ester or carboxylic acid comprising an aromatic ring or heteroaromatic ring by the action of a condensing agent or catalyst to form a star-shaped copolymer; and (2) dissolving the star-shaped copolymer of step (1) in a vehicle and allowing the hydrogel to spontaneously form at around body temperature (37° C.).

In some embodiments, the condensing agent is selected from one or more of dicyclohexylcarbodiimide, diisopropylcarbodiimide and 1-(3-dimethylaminopropyl)-3-ethylcarbodiimide.

In some embodiments, the catalyst is selected from one or more of 4-dimethylaminopyridine, 1-hydroxy benzotriazole and 4-pyrrolidinylpyridine.

The present disclosure further provides a method for enhancing the solubility of a drug or bioactive agent comprising mixing the drug or bioactive agent into the thermosensitive polymer or compound or composition or hydrogel of the present disclosure.

The present disclosure further provides a method for releasing a drug or bioactive agent in a sustained or controlled manner comprising mixing the drug or bioactive agent into the thermosensitive polymer or compound or composition or hydrogel of the present disclosure.

The present disclosure further provides a method for enhancing the stability of a drug or bioactive agent comprising mixing the drug or bioactive agent into the thermosensitive polymer or compound or composition or hydrogel of the present disclosure.

The present disclosure further provides a method for treating and/or preventing a disease comprising: a step of injecting the thermosensitive polymer or compound or composition or hydrogel of the present disclosure into a physiological environment. In alternative embodiments, the disease in the present disclosure is selected from the group consisting of, but is not limited to, a vascular disease, a neoplastic disease, diabetes, an immune system disease, and the like.

The dose used in the treatment and/or prevention method of the present disclosure generally varies depending on the severity of the disease, the body weight of the patient, and the relative efficacy of the compound. However, as a general instruction, a suitable unit dose may be 0.1-1000 mg.

The thermosensitive polymer or compound or composition or pharmaceutical composition or hydrogel of the present disclosure is thermosensitive: it can be a solution when the temperature is room temperature or below room temperature and it can transition into a gel when the temperature is human body temperature. The thermosensitive polymer or compound or composition or hydrogel of the present disclosure can be blended with a drug or bioactive agent so that the drug or bioactive agent can be conveniently and efficiently injected (including but not limited to minimally invasive routes such as a catheter or needle) into a specific site (e.g., directionally administered to a surgical defect site, in the vicinity of a surgical diseased site or to the surrounding subcutaneous tissues).

The thermosensitive polymer or compound or composition or pharmaceutical composition or hydrogel of the present disclosure forms a gel in situ at body temperature as a long-acting sustained-release formulation, which allows for a stable and slow release of the drug or bioactive agent by the combined action of drug diffusion and gel degradation.

After the solution of the thermosensitive polymer or compound or combination or pharmaceutical composition or hydrogel of the present disclosure arrives at a focus, the fluidity of the solution enables the shape of the formed gel to better fit the shape of the defect site, avoiding the formation of gaps or hard bumps between material and tissue.

After the solution of the thermosensitive polymer or compound or composition or pharmaceutical composition or hydrogel of the present disclosure is well mixed with a drug, a bioactive agent, cells, or the like and then injected into the body, it forms a gel, and the gel forms a drug repository in drug delivery or a temporary scaffold for cell proliferation, differentiation and regeneration in tissue engineering.

The thermosensitive polymer or compound or composition or pharmaceutical composition or hydrogel of the present disclosure is a biodegradable or bioabsorbable material that can break down or degrade in vivo to form non-toxic components, is safe for patients, causes as little irritation as possible to its surrounding tissues, and is a compatible medium for drugs.

The thermosensitive polymer or compound or composition or pharmaceutical composition or hydrogel of the present disclosure has a special topological structure and has a higher degree of winding of chain segments than a linear polymer; therefore, the drug embedded in it is less prone to dissolution.

The thermosensitive polymer or compound or composition or pharmaceutical composition or hydrogel of the present disclosure has a smaller hydrodynamic volume and a smaller viscosity in solution than a single linear polymer of the same molecular weight and therefore is less likely to be blocked in blood.

The thermosensitive polymer or compound or composition or pharmaceutical composition of the present disclosure easily self-assembles into micelles. After the formation of the micelles, forming bridging structures between the micelles is easier, and then a thermosensitive hydrogel with better resistance to swelling is formed.

In another aspect, where the configuration is not specified, the thermosensitive polymer or compound of the present disclosure can be present in specific geometric or stereoisomeric forms. The present disclosure contemplates all such thermosensitive polymers or compounds, including cis and trans isomers, (−)- and (+)-enantiomers, (R)- and (S)-enantiomers, diastereomers, (D)-isomer, (L)-isomer, and racemic mixtures and other mixtures thereof, such as enantiomerically or diastereomerically enriched mixtures, all of which are within the scope of the present disclosure. Additional asymmetric carbon atoms may be present in substituents such as an alkyl group. Unless otherwise specified, all such isomers and mixtures thereof are included within the scope of the present disclosure.

The thermosensitive polymer or compound of the present disclosure may be asymmetric; for example, the compounds have one or more stereoisomers. Where the configuration is not specified, all stereoisomers are included, for example, enantiomers and diastereomers. The thermosensitive polymer or compound of the present disclosure containing asymmetric carbon atoms can be isolated in optically active pure form or in racemic form. The optically active pure form can be isolated from a racemic mixture or synthesized using chiral starting materials or chiral reagents.

In the chemical structure of the compound of the present disclosure, a bond "" represents an unspecified configuration; that is, if chiral isomers exist in the chemical structure, the bond "" may be "" or "", or contains both the configurations of "" and "". All of the above structural formulas are drawn as certain isomeric forms for the sake of simplicity. However, where no configuration is specified, the present disclosure may include all isomers, such as rotamers, geometric isomers, diastereomers, racemates and enantiomers. In the chemical structure of the compound of the present disclosure, a bond "" does not specify a configuration—that is, the configuration for the bond "" can be an E configuration or a Z configuration, or includes both the E configuration and the Z configuration.

Optically active (R)- and (S)-enantiomers, and D- and L-isomers can be prepared by chiral synthesis, chiral reagents or other conventional techniques. If one enantiomer of a certain thermosensitive polymer or compound of the present disclosure is desired, it may be prepared by asymmetric synthesis or derivatization with a chiral auxiliary, wherein the resulting mixture of diastereomers is separated and the auxiliary group is cleaved to provide the pure desired enantiomer. Alternatively, when the molecule contains a basic functional group (e.g., amino) or an acidic functional group (e.g., carboxyl), salts of diastereomers are formed with an appropriate optically active acid or base, followed by resolution of diastereomers by conventional methods known in the art, and the pure enantiomers are obtained by recovery. In addition, separation of enantiomers and diastereomers is generally accomplished by chromatography using a chiral stationary phase, optionally in combination with chemical derivatization (e.g., carbamate formation from amines).

The disclosure further includes isotopically-labeled compounds which are identical to those recited herein but have one or more atoms replaced by an atom having an atomic mass or mass number different from the atomic mass or mass number usually found in nature. Examples of isotopes that can be incorporated into the compound of the present disclosure include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Unless otherwise specified, when a position is specifically assigned deuterium (D), the position should be construed as deuterium with an abundance that is at least 1000 times greater than the natural abundance of deuterium (which is 0.015%) (i.e., at least 10% deuterium incorporation). The compounds of examples comprise deuterium having an abundance that is greater than at least 1000 times the natural abundance, at least 2000 times the natural abundance, at least 3000 times the natural abundance, at least 4000 times the natural abundance, at least 5000 times the natural abundance, at least 6000 times the natural abundance, or higher times the natural abundance. The present disclosure further comprises various deuterated forms of the compounds. Each available hydrogen atom connected to a carbon atom may be independently replaced by a deuterium atom. Those skilled in the art can synthesize the compounds in deuterated form by reference to the relevant literature. Commercially available deuterated starting materials can be used in preparing the deuterated compounds, or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like.

TERMS AND DEFINITIONS

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

"Optionally" or "optional" means that the event or circumstance subsequently described may, but does not necessarily, occur and that the description includes instances where the event or circumstance occurs or does not occur. For example, "$C_{1-6}$ alkyl that is optionally substituted with a halogen or cyano" means that the halogen or cyano may, but does not necessarily, exist, and the description includes the instance where alkyl is substituted with a halogen or cyano and the instance where alkyl is not substituted with a halogen or cyano.

The term "linear" means that the polymer has no or essentially no branching units and thus the number of termini of the polymer backbone is 2.

The term "star-shaped" means that the polymer backbone has at least one branching site and thus has at least 3, e.g., 3, 4, 5, 6, 7, 8, 9 or 10, termini.

The term "biodegradable" means that the polymer can chemically break down or degrade within the body to form non-toxic components. The rate of degradation can be the same or different from the rate of drug release.

The term "polymer" refers to a molecule containing multiple covalently connected monomer units, and may include branched, dendrimeric and star-shaped polymers as well as linear polymers. The term also includes homopolymers, copolymers and combinations thereof, e.g., random copolymers, block copolymers and graft copolymers, as well as uncrosslinked polymers and slightly to moderately to substantially crosslinked polymers.

The term "temperature of the solution-gel phase transition" is also sometimes referred to as lower critical gelation temperature or gelation temperature, and they are used interchangeably and refer to a temperature where a polymer solution transitions into a gel as the temperature gradually increases.

The term "thermosensitive" or "thermosensitivity" refers to a property that when the temperature of the solution is higher than the solution-gel phase transition temperature of the polymer, the increase in temperature induces a rearrangement and alignment of the polymer chains, leading to gelation into a three-dimensional structure: the viscosity of the polymer solution spontaneously increases, and in many cases the copolymer transitions into a semi-solid gel. All interactions leading to gels are physical reactions, which do not involve the formation or breaking of covalent bonds.

The terms "polymer solution", "aqueous polymer solution", "hydrogel solution", and the like, refer to a solution that, when used for the polymer contained in the solution, is maintained at a temperature below the gelation temperature of the polymer.

The terms "gel" and "hydrogel" are used interchangeably and refer to a swollen, water-containing network of finely-dispersed polymer chains that are water-insoluble, where the polymeric molecules are in the external or dispersion external phase and water (or an aqueous solution) forms the internal or dispersion phase. For example, a polymer solution or hydrogel solution spontaneously forms a semi-solid phase when the temperature is raised to or above the gelation temperature of the polymer.

The terms "polyethylene glycol" and "PEG" are also sometimes referred to as poly(ethylene oxide) (PEO) or poly(oxyethylene), and the terms can be used interchangeably for the purposes of the present disclosure.

The term "polylactic acid-glycolic acid copolymer" or "PLGA", also sometimes referred to as "poly(lactide-co-glycolide)", refers to a copolymer obtained by the condensation copolymerization of lactic acid and glycolic acid or the ring opening polymerization of α-hydroxy acid precursors, such as lactide or glycolide. The terms "lactide", "lactate", "glycolide" and "glycolate" are used interchangeably herein. In the present disclosure, PLGA may be drawn as form E or form F. Form E and form F are used interchangeably herein and both are within the scope of the present disclosure:

Form E

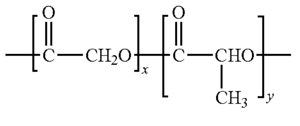

and

Form F

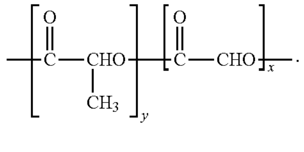

The terms "polylactic acid-polycaprolactone copolymer" and "PCLA", also sometimes referred to as "poly(ε-caprolactone-co-lactide)", are used interchangeably herein. In the present disclosure, PCLA may be drawn as form G or form H. Form G and form H are used interchangeably herein and both are within the scope of the present disclosure:

Form G

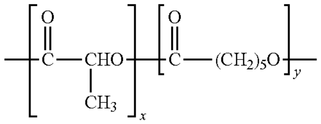

and

Form H

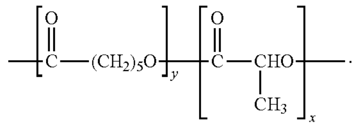

The terms "about" and "approximately" mean that a numerical value is within an acceptable error range for the specific value determined by those of ordinary skill in the art, and the numerical value depends in part on how the value is measured or determined (i.e., the limits of the measurement system). For example, "about" may mean a standard deviation within 1 or more than 1. Alternatively, "about" or "comprising essentially" may mean a range of at most 20%, e.g., a change of between 1% and 15%, between 1% and 10%, between 1% and 5%, between 0.5% and 5%, or between 0.5% and 1%. In the present disclosure, every instance where a number or numerical range is preceded by the term "about" also includes an embodiment of the given number. Unless otherwise stated, when a specific value is provided in the present application and claims, the meaning of "about" or "substantially comprising" should be assumed to be within an acceptable error range for that specific value.

The term "biocompatible" describes substances which, in the amounts used, are non-toxic, chemically inert, and substantially non-immunogenic in patients and which are substantially insoluble in blood. It describes materials, along with any metabolites or degradation products thereof, that are generally non-toxic to the recipient and do not cause any significant adverse effects to the recipient. Generally speaking, biocompatible materials are materials which do not elicit a significant inflammatory, immune or toxic response when administered to an individual.

The term "alkyl" refers to a saturated aliphatic hydrocarbon group which is a linear or branched group containing 1 to 20 carbon atoms, preferably an alkyl group containing 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl. 1,2-dimethylpropyl, 2,2-dimethylpropyl. 1-ethylpropyl, 2-methylbutyl, 3-methylbutyl, n-hexyl, 1-ethyl-2-methylpropyl. 1,1,2-trimethylpropyl, 1,1-dimethylbutyl, 1,2-dimethylbutyl. 2,2-dimethylbutyl, 1,3-dimethylbutyl. 2-ethylbutyl. 2-methylpentyl, 3-methylpentyl. 4-methylpentyl, 2,3-dimethylbutyl, n-heptyl, 2-methylhexyl. 3-methylhexyl, 4-methylhexyl, 5-methylhexyl, 2,3-dimethylpentyl. 2,4-dimethylpentyl. 2,2-dimethylpentyl. 3,3-dimethylpentyl, 2-ethylpentyl, 3-ethylpentyl, n-octyl. 2,3-dimethylhexyl. 2,4-dimethylhexyl. 2,5-dimethylhexyl. 2,2-dimethylhexyl, 3,3-dimethylhexyl. 4,4-dimethylhexyl. 2-ethylhexyl. 3-ethylhexyl, 4-ethylhexyl. 2-methyl-2-ethylpentyl. 2-methyl-3-ethylpentyl, n-nonyl. 2-methyl-2-ethylhexyl, 2-methyl-3-ethylhexyl. 2,2-diethylpentyl, n-decyl, 3,3-diethylhexyl. 2,2-diethylhexyl, and various branched isomers thereof, and the like. More preferred is an alkyl group containing 1 to 6 carbon atoms; non-limiting examples include methyl, ethyl, n-propyl, isopropyl, n-butyl, isobutyl, tert-butyl, sec-butyl, n-pentyl, 1,1-dimethylpropyl, 1,2-dimethylpropyl. 2,2-dimethylpropyl, 1-ethylpropyl, 2-methylbutyl. 3-methylbutyl, n-hexyl, 1-ethyl-2-methylpropyl. 1,1,2-trimethylpropyl. 1,1-dimethylbutyl, 1,2-dimethylbutyl. 2,2-dimethylbutyl, 1,3-dimethylbutyl. 2-ethylbutyl, 2-methylpentyl, 3-methylpentyl. 4-methylpentyl, 2,3-dimethylbutyl, and the like. Alkyl may be substituted or unsubstituted, and when it is substituted, the substituent may be substituted at any available point of attachment, and the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and carboxy late group.

The term "alkoxy" refers to —O-(alkyl) and —O-(unsubstituted cycloalkyl), wherein the alkyl is as defined above. Non-limiting examples of alkoxy include: methoxy, ethoxy, propoxy, butoxy, cyclopropyloxy, cyclobutoxy, cyclopentyloxy and cyclohexyloxy. Alkoxy may be optionally substituted or unsubstituted, and when it is substituted, the substituent is preferably one or more groups independently selected from the group consisting of halogen, deuterium, hydroxy, oxo, nitro, cyano, $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy, and 5- to 6-membered aryl or heteroaryl, and the $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy and 5- to 6-membered aryl or heteroaryl are optionally substituted with one or more groups selected from the group consisting of halogen, deuterium, hydroxy, oxo, nitro and cyano. Similarly, "alkynyloxy", "alkenyloxy", "cycloalkoxy", "heterocycloalkoxy" and "cycloalkenyloxy" are as defined above for "alkoxy".

The term "alkenyl" refers to a linear or branched non-aromatic hydrocarbon group containing at least one carbon-carbon double bond and having 2-10 carbon atoms. Up to 5 carbon-carbon double bonds can be present in such groups. For example, "$C_2$-$C_6$" alkenyl is defined as alkenyl having 2-6 carbon atoms. Examples of alkenyl include, but are not limited to: ethenyl, propenyl, butenyl and cyclohexenyl. The linear, branched or cyclic portion of alkenyl may contain a double bond and is optionally mono-, di-, tri-, tetra- or penta-substituted at any position as permitted by normal valency.

The term "alkynyl" refers to a linear or branched hydrocarbon group containing 2-10 carbon atoms and containing at least one carbon-carbon triple bond. Up to 5 carbon-carbon triple bonds can be present. Thus, "$C_2$-$C_6$ alkynyl" refers to alkynyl having 2-6 carbon atoms. Examples of alkynyl include, but are not limited to: ethynyl, 2-propynyl and 2-butynyl. The linear or branched portion of alkynyl may contain a triple bond as permitted by normal valency and is optionally mono-, di-, tri-, tetra- or penta-substituted at any position as permitted by normal valency.

The term "cycloalkyl" or "carbocycle" refers to a saturated or partially unsaturated monocyclic or polycyclic hydrocarbon substituent. The cycloalkyl ring contains 3 to 20 carbon atoms, preferably 3 to 7 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, and the like. Polycyclic cycloalkyl includes spiro cycloalkyl, fused cycloalkyl and bridged cycloalkyl. Cycloalkyl may be substituted or unsubstituted, and when it is substituted, the substituent may be substituted at any available point of attachment, and the substituent is preferably one or more groups independently selected from the group consisting of halogen, deuterium, hydroxy, oxo, nitro, cyano, $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy, and 5- to 6-membered aryl or heteroaryl, and the $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy and 5- to 6-membered aryl or heteroaryl are optionally substituted with one or more groups selected from the group consisting of halogen, deuterium, hydroxy, oxo, nitro and cyano.

The cycloalkyl ring may be fused to an aryl or heteroaryl ring, wherein the ring attached to the parent structure is cycloalkyl; non-limiting examples include indanyl, tetrahydronaphthyl, benzocycloheptyl, and the like. The term "heterocycloalkyl" or "heterocycle" or "heterocyclyl" refers to a saturated or partially unsaturated monocyclic or polycyclic cyclohydrocarbon substituent containing 3 to 20 ring atoms, wherein one or more of the ring atoms are heteroatoms selected from the group consisting of nitrogen, oxygen and $S(O)_m$ (where m is an integer from 0 to 2), excluding a cyclic moiety of —O—O—, —O—S— or —S—S—, and the remaining ring atoms are carbon atoms. It preferably contains 3 to 12 ring atoms, 1 to 4 of which are heteroatoms: more preferably, it contains 3 to 7 ring atoms. Non-limiting examples of monocyclic heterocycloalkyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, and the like. Polycyclic heterocycloalkyl includes spiro heterocyclyl, fused heterocyclyl and bridged heterocycloalkyl. Non-limiting examples of "heterocycloalkyl" include:

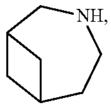, 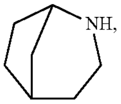, 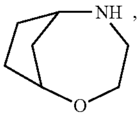, 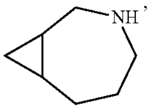,

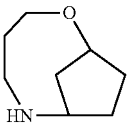, 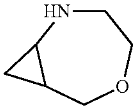, 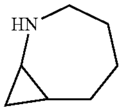, 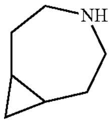,

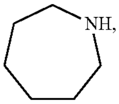, 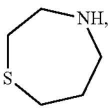, 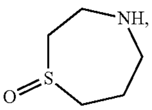, 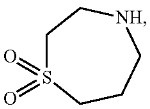,

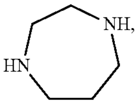, 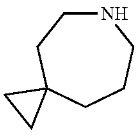, 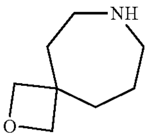,

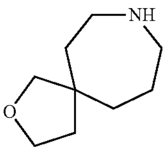, 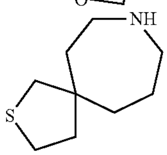,

-continued

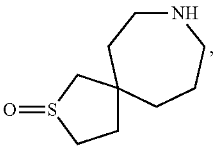, 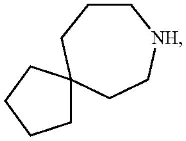,

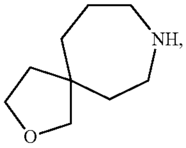, 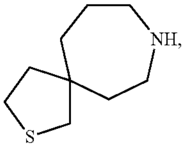,

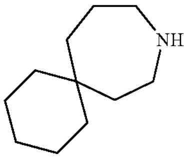 and 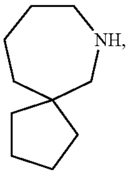, and the like.

The heterocycloalkyl ring may be fused to an aryl or heteroaryl ring, wherein the ring attached to the parent structure is heterocycloalkyl; its non-limiting examples include:

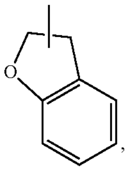, 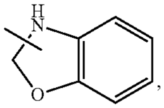, 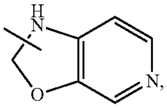,

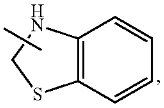, and the like.

Heterocycloalkyl may be optionally substituted or unsubstituted, and when it is substituted, the substituent is preferably one or more groups independently selected from the group consisting of halogen, deuterium, hydroxy, oxo, nitro, cyano, $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy, and 5- to 6-membered aryl or heteroaryl, and the $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy and 5- to 6-membered aryl or heteroaryl are optionally substituted with one or more groups selected from the group consisting of halogen, deuterium, hydroxy, oxo, nitro and cyano.

The term "aryl" refers to a 6- to 14-membered, preferably 6- to 12-membered, carbon monocyclic or fused polycyclic (i.e., rings sharing a pair of adjacent carbon atoms) group having a conjugated x-electron system, such as phenyl and naphthyl. The aryl ring may be fused to a heteroaryl, heterocycloalkyl or cycloalkyl ring, wherein the ring attached to the parent structure is the aryl ring; its non-limiting examples include:

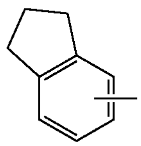, 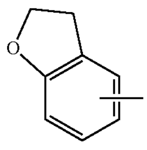, 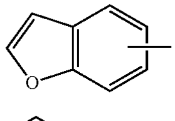, 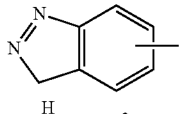, 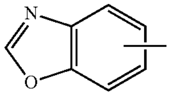, 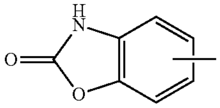, 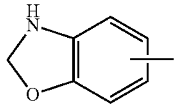, 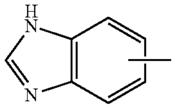, 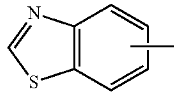, 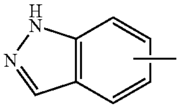, 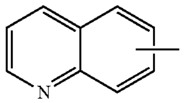, 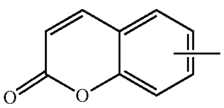 and 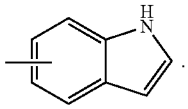.

Aryl may be substituted or unsubstituted, and when it is substituted, the substituent is preferably one or more groups independently selected from the group consisting of halogen, deuterium, hydroxy, oxo, nitro, cyano, $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy, and 5- to 6-membered aryl or heteroaryl, and the $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy and 5- to 6-membered aryl or heteroaryl are optionally substituted with one or more groups selected from the group consisting of halogen, deuterium, hydroxy, oxo, nitro and cyano.

The term "heteroaryl" refers to a heteroaromatic system containing 1 to 4 heteroatoms and 5 to 14 ring atoms, wherein the heteroatoms are selected from the group consisting of oxygen, sulfur and nitrogen. Heteroaryl is preferably 6- to 12-membered, and is more preferably 5- or 6-membered. For example, its non-limiting examples include: imidazolyl, furanyl, thienyl, thiazolyl, pyrazolyl, oxazolyl, isoxazolyl, pyrrolyl, tetrazolyl, pyridinyl, pyrimidinyl, thiadiazole, pyrazinyl, triazolyl, indazolyl, benzimidazolyl,

, 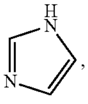, 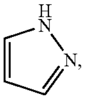, and the like.

The heteroaryl ring may be fused to an aryl, heterocycloalkyl or cycloalkyl ring, wherein the ring attached to the parent structure is the heteroaryl ring; its non-limiting examples include:

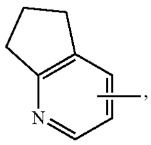, 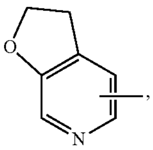, 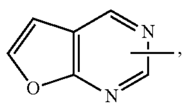, 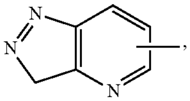, 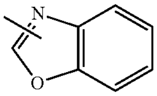, 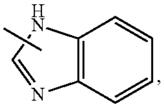, 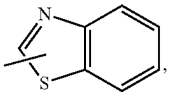, 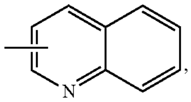, and 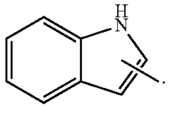.

Heteroaryl may be optionally substituted or unsubstituted, and when it is substituted, the substituent is preferably one or more groups independently selected from the group consisting of halogen, deuterium, hydroxy, oxo, nitro, cyano, $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy, and 5- to 6-membered aryl or heteroaryl, and the $C_{1-6}$ alkyl, $C_{1-6}$ alkoxy, $C_{2-6}$ alkenyloxy, $C_{2-6}$ alkynyloxy, $C_{3-6}$ cycloalkoxy, 3- to 6-membered heterocycloalkoxy, $C_{3-8}$ cycloalkenyloxy and 5- to 6-membered aryl or heteroaryl are optionally substituted with one or more groups selected from the group consisting of halogen, deuterium, hydroxy, oxo, nitro and cyano.

The suffix "-ene" on the name of a chemical moiety refers to any divalent, carbon-containing species, including, but not limited to, alkylene, alkenylene, alkynylene, cycloalkylene, heterocycloalkylene, arylene, heteroarylene, cyclylene and heterocyclylene. When chemically feasible, the two attachments to the divalent moiety can occur on the same atom or different atoms.

"Alkylene" refers to the moiety of an alkane molecule remaining after removal of 2 hydrogen atoms, and includes linear and branched ylene groups of 1 to 20 carbon atoms. Non-limiting examples of alkylene containing 1 to 6 carbon atoms include methylene ($—CH_2—$), ethylene (e.g., $—CH_2CH_2—$ or $—CH(CH_3)—$), propylene (e.g. $—CH_2CH_2CH_2—$ or $—CH(CH_2CH_3)—$), and butylene (e.g., $—CH_2CH_2CH_2CH_2—$). Alkylene may be substituted or unsubstituted, and when it is substituted, the substituent may be substituted at any available point of attachment, and the substituent is preferably one or more groups independently selected from the group consisting of halogen, deuterium, hydroxy, nitro, cyano and amino.

The term "alkenylene" refers to an alkene having two monovalent radical centers derived by the removal of two hydrogen atoms from the same or two different carbon atoms of a parent alkene. Non-limiting examples of alkenylene include, but are not limited to, $—CH{=}CH—$, $—CH{=}CHCH_2—$, $—CH{=}CHCH_2CH_2—$, $—CH_2CH{=}CHCH_2—$, and the like. Alkenylene may be substituted or unsubstituted, and when it is substituted, the substituent is preferably one or more, preferably one to five, and more preferably one to three, substituents independently selected from the group consisting of alkyl, alkenyl, alkynyl, alkoxy, alkylsulfo, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio.

The term "alkynylene" refers to an alkynyl group having two monovalent radical centers derived by the removal of two hydrogen atoms from the same or two different carbon atoms of a parent alkyne. Typical alkynylene groups include, but are not limited to, ethynylene (—C≡C—), propargylene ($—CH_2C≡C—$) and 1-pentynylene ($—CH_2CH_2CH_2C≡C—$).

The term "arylene" refers to an aryl group having two monovalent radical centers derived by the removal of two hydrogen atoms from the same or two different carbon atoms of a parent aryl group.

The term "heteroarylene" refers to a heteroaryl group, as defined above, having two monovalent radical centers derived by the removal of two hydrogen atoms from the same or two different carbon atoms or the removal of a hydrogen from one carbon atom and the removal of a hydrogen atom from one nitrogen atom of a parent heteroaryl group.

The term "heteroalkylene" refers to an alkylene group, as defined herein, in which one or more carbon atoms are replaced with an oxygen, sulfur or nitrogen atom.

The term "cycloalkylene" refers to a group formed by formally eliminating two hydrogen atoms from a saturated or partially unsaturated monocyclic or polycyclic hydrocarbon, which contains 3 to 20 carbon atoms, preferably 3 to 12 carbon atoms: more preferably, the monocyclic cycloalkylene ring contains 3 to 10 carbon atoms, and most preferably 3 to 6 carbon atoms. Non-limiting examples of monocyclic cycloalkylene include cyclopropylene, cyclobutylene, cyclopentylene, cyclohexylene, cycloheptylene, cyclooctylene, 1,2-cyclopropylene, 1,3-cyclobutylene, 1,4-cyclohexylene, and the like. Polycyclic cycloalkylene groups include spiro, fused and bridged cycloalkylene groups.

The term "heterocycloalkylene" refers to a divalent group formed from heterocyclyl and two substituents on a single ring carbon.

The term "hydroxy" refers to the —OH group.

The term "halogen" refers to fluorine, chlorine, bromine or iodine.

The term "haloalkyl" refers to an alkyl group substituted with halogen, wherein the alkyl group is as defined above.

The term "haloalkoxy" refers to an alkoxy group, as defined in the present disclosure, optionally substituted with one or more halogen atoms.

The term "cyano" refers to —CN.

The term "nitro" refers to $—NO_2$.

The term "oxo" refers to the =O group; for example, a carbon atom is connected to an oxygen atom by a double bond to form a ketone or aldehyde group.

The term "amino" refers to $—NH_2$.

The term "substituted" means that any one or more hydrogen atoms on the specified atom, usually a carbon, oxygen or nitrogen atom, are replaced with any group as defined herein, provided that the normal valency of the specified atom is not exceeded, and that the substitution results in a stable compound. Non-limiting examples of substituents include $C_1$-$C_6$ alkyl, $C_2$-$C_6$ alkenyl, $C_2$-$C_6$ alkynyl, cyano, hydroxy, oxo, carboxyl, cycloalkyl, cycloalkenyl, heterocyclyl, heteroaryl, aryl, ketone, alkoxycarbonyl, aryloxycarbonyl, heteroaryloxy carbonyl, or halogen (e.g., F, Cl, Br or I). When the substituent is a ketone or oxo (i.e., =O), two (2) hydrogen atoms on the atom are replaced.

"Substituted with one or more . . . " means that it may be substituted with a single substituent or multiple substituents. In the case of substitution with multiple substituents, there may be a plurality of identical substituents, or one combination of or a plurality of combinations of different substituents.

The term "effective amount" or "effective dosage" refers to the amount of a drug, a compound or a pharmaceutical composition necessary to obtain any one or more beneficial or desired therapeutic results. For preventive use, the beneficial or desired results include elimination or reduction of risk, reduction of severity or delay of the onset of a disorder, including the biochemistry, histology and/or behavioral symptoms of the disorder, complications thereof and intermediate pathological phenotypes that appear during the progression of the disorder. For therapeutic applications, the beneficial or desired results include clinical results, such as reducing the incidence of various disorders related to the target gene, target mRNA or target protein or alleviating one or more symptoms of the disorder, reducing the dosage of other agents required to treat the disorder, enhancing the therapeutic effect of another agent, and/or delaying the progression of disorders related to the target gene, target mRNA or target protein in the patient.

The term "pharmaceutical composition" refers to a mixture containing one or more of the compounds or the physiologically/pharmaceutically acceptable salts or prodrugs thereof described herein, and other chemical components, for example, physiologically/pharmaceutically acceptable carriers and excipients. The pharmaceutical composition is intended to promote the administration to an organism, so as to facilitate the absorption of the active ingredient, thereby exerting biological activity.

The term "pharmaceutically acceptable excipient" includes, but is not limited to, any auxiliary, carrier, excipient, glidant, sweetener, diluent, preservative, dye/colorant, flavoring agent, surfactant, wetting agent, dispersant, suspending agent, stabilizer, isotonic agent, solvent or emulsifier that has been approved by the U.S. Food and Drug Administration as acceptable for use in humans or livestock animals.

When a trade name is used in the present disclosure, the applicant intends to include the formulation of the commercial product under the trade name, and the non-patent drug and active drug component of the commercial product under the trade name.

DETAILED DESCRIPTION

Figure 1:
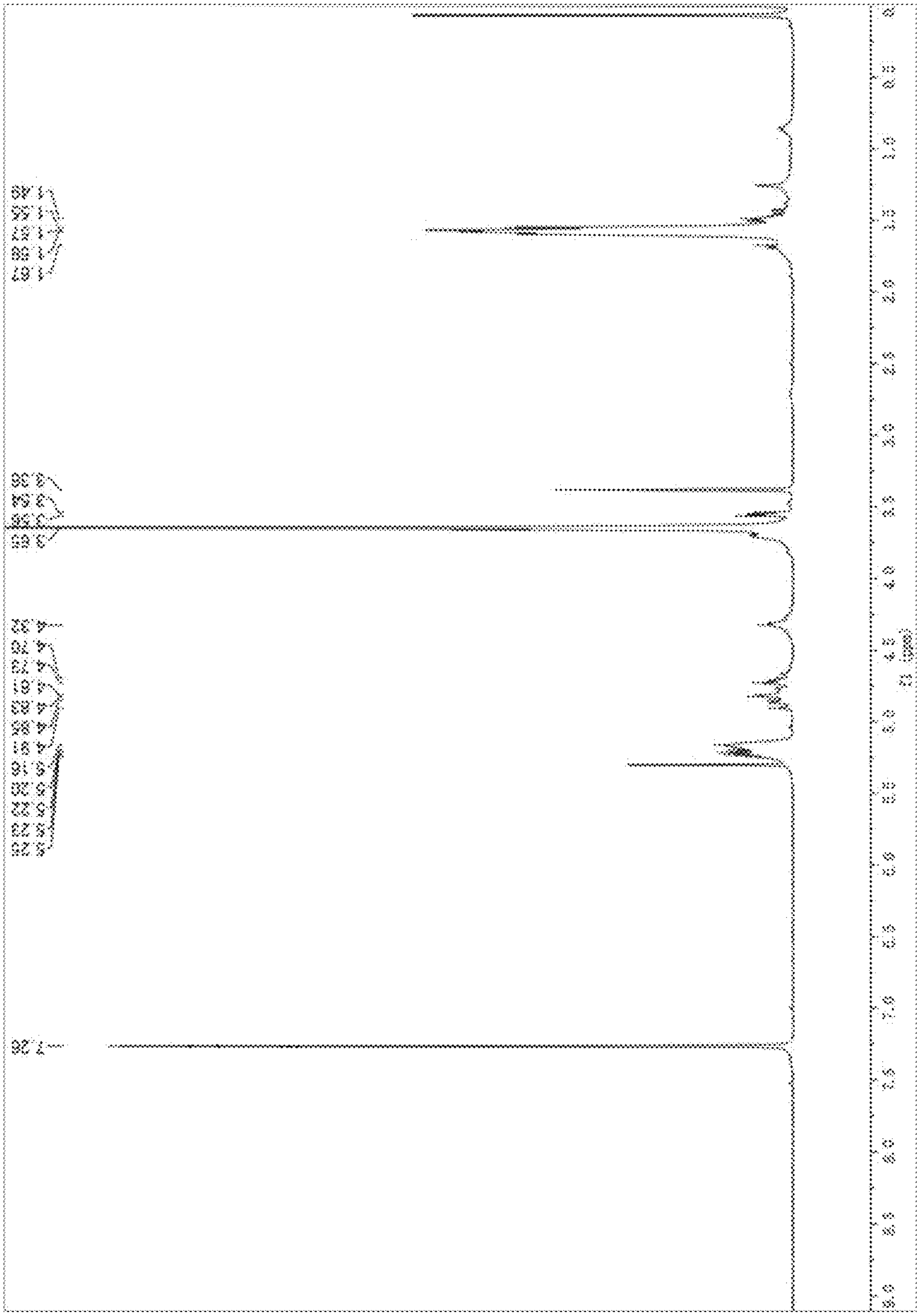
FIG. 1 shows a $^1$H-NMR spectrum of a diblock polymer mPEG-PLGA.

The present disclosure is further described below using examples, and these examples do not limit the scope of the disclosure.

The structures of compounds were determined by nuclear magnetic resonance (NMR). NMR shifts (δ) are given in $10^{-6}$ (ppm). NMR analysis was performed on a Bruker AVANCE-400 nuclear magnetic resonance instrument, with deuterated chloroform ($CDCl_3$) as a solvent and tetramethylsilane (TMS) as an internal standard.

Gel permeation chromatography (GPC) analysis was performed on a Waters 2695 GPC gel permeation chromatograph, with tetrahydrofuran as a mobile phase.

High performance liquid chromatography (HPLC) analysis was performed on an Agilent HPLC 1200 DAD high performance liquid chromatograph.

Known starting materials described herein may be synthesized using or according to methods known in the art, or may be purchased from Aldrich Chemical Company, Adamas Reagent, Jinan Daigang Biomaterial Co., Ltd., etc.

In the examples, reactions can all be performed in an argon atmosphere or a nitrogen atmosphere unless otherwise specified.

The argon atmosphere or nitrogen atmosphere means that the reaction flask is connected to a balloon containing about 1 L of argon or nitrogen.

In the examples, a solution was an aqueous solution unless otherwise specified.

In the examples, the reaction temperature was room temperature, i.e., 20° C.-30° C., unless otherwise specified.

Example 1

1.1. Synthesis of Amphiphilic Diblock Copolymer mPEG-PLGA 5 g of mPEG 550 was weighed out and added to a 100 mL round-bottom flask, and dehydrated under vacuum for 1 h with stirring at 130° C. After the temperature was reduced to room temperature, 8.14 g of D,L-lactide and 1.86 g of glycolide were added, and a solution of stannous octoate (15 mg) in dimethylbenzene was added. Dimethylbenzene was removed by 2 h of vacuumization. The mixture was left to react in a 140° C. oil bath in a nitrogen atmosphere for 16 h. Then the reaction mixture was dissolved in dichloromethane, and a polymer was precipitated using petroleum ether. The polymer was dried in vacuo to give the final product, namely the diblock polymer mPEG-PLGA. The block polymer was characterized by gel permeation chromatography (GPC, polyethylene glycol as standard) and found to have a number-average molecular weight (Mn) of 1557 and a weight-average molecular weight (Mw) of 2109, and therefore a molecular weight distribution coefficient (Mw/Mn) of 1.35. This copolymer is soluble in water and can have a reversible solution-gel transition as the temperature increases.

The structure of the diblock polymer mPEG-PLGA is:

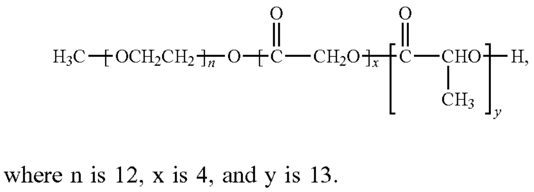

where n is 12, x is 4, and y is 13.

The block polymer was characterized by gel permeation chromatography (GPC, polyethylene glycol as standard) and found to have a number-average molecular weight (Mn) of 1557 and a weight-average molecular weight (Mw) of 2109, and therefore a molecular weight distribution coefficient (Mw/Mn) of 1.35. This copolymer is soluble in water and can have a reversible solution-gel transition as the temperature increases.

FIG. 1 shows a 1H-NMR spectrum of the polymer mPEG-PLGA, where the hydrogen at 3.65 ppm is from the methylene in mPEG, the hydrogen at 3.38 ppm is from the methyl in mPEG, the hydrogen at 4.8 ppm is from the methylene in glycolide, and the hydrogen at 5.1 ppm is from the methine in D,L-lactide. According to areas calculated by integration, the results agree with the ratio of the starting materials.

1.2. Synthesis of Star-Shaped Multi-Arm Polymer PMDA-mPEG-PLGA 4 g of the diblock copolymer mPEG-PLGA was added to a 100 mL round-bottom flask and dissolved in 28 mL of dichloromethane, and then 124 mg of pyromellitic dianhydride, 1.719 g of N,N-diisopropylcarbodiimide and 166 mg of 4-dimethylaminopyridine were sequentially added. The mixture was left to react in a 25° C. oil bath for 24 h. Then a polymer was precipitated using absolute ethanol. The polymer was dried in vacuo to give the final product, namely the star-shaped multi-arm polymer PMDA-mPEG-PLGA. Gel permeation chromatography (GPC, polyethylene glycol as standard) analysis showed that the above polymer has a number-average molecular weight (Mn) of 5112 and a weight-average molecular weight (Mw) of 5836, and therefore a molecular weight distribution coefficient (Mw/Mn) of 1.14. The structure of the star-shaped multi-arm polymer PMDA-mPEG-PLGA is:

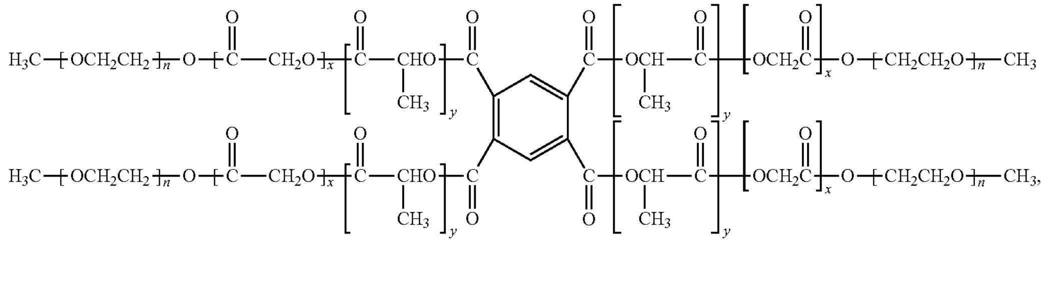

where n is 12, x is 4, and y is 16.

Figure 2:
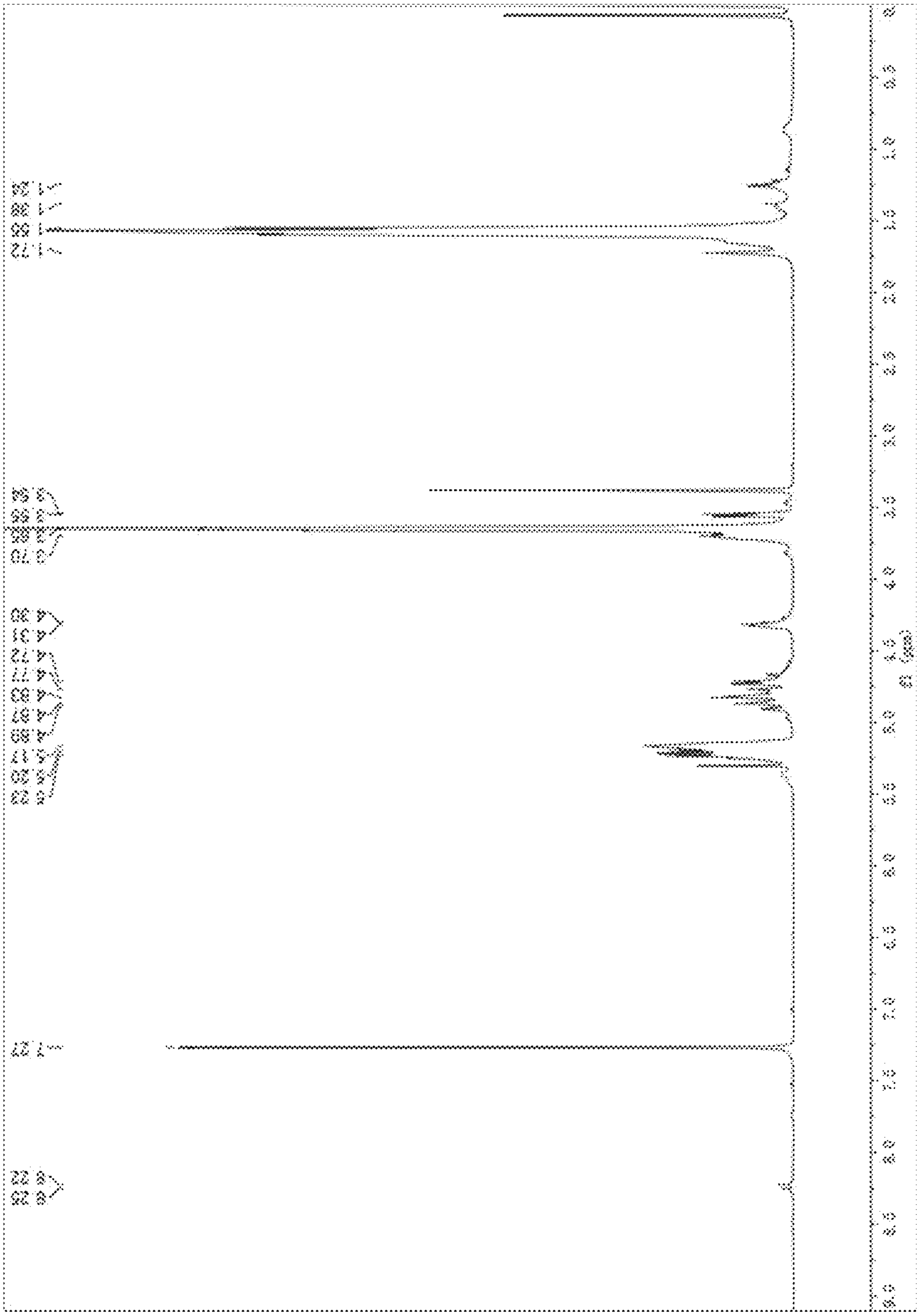
FIG. 2 shows a $^1$H-NMR spectrum of a star-shaped multi-arm polymer PMDA-mPEG-PLGA.

FIG. 2 shows a 1H-NMR spectrum of the star-shaped multi-arm polymer PMDA-mPEG-PLGA, where in addition to the hydrogens of the diblock polymer described above, a new peak can be seen at 8.2 ppm. The peak belongs to the hydrogen on the benzene ring in PMDA, suggesting that the star-shaped polymer PMDA-mPEG-PLGA has been successfully synthesized.

A proper amount of the star-shaped copolymer was weighed out and dissolved in water to form a 20 wt % polymer solution and a 25 wt % polymer solution. The results of a tube-inverting test show that the obtained solutions of the star-shaped copolymer can have a solution-gel phase transition at physiological temperature (37° C.).

Figure 3:
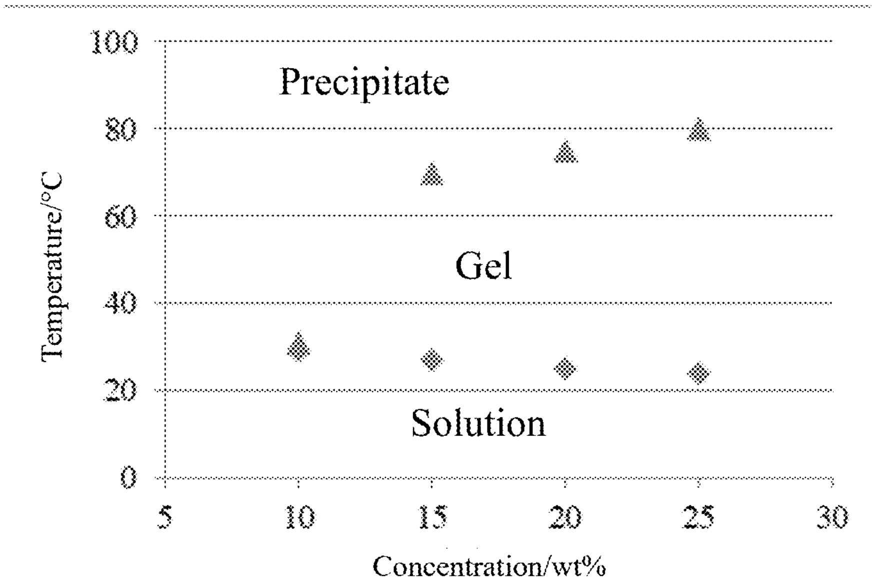
FIG. 3 shows a phase diagram of the solution-gel transition of the star-shaped multi-arm polymer PMDA-mPEG-PLGA, where the triangles indicate temperatures at which precipitation occurs in polymer gels of certain concentrations, and the *rhombi* indicate temperatures at which polymer solutions of certain concentrations transition into gels.

FIG. 3 shows a phase diagram of the solution-gel transition of the star-shaped multi-arm polymer PMDA-mPEG-PLGA. A proper amount of the star-shaped multi-arm polymer was weighed out and dissolved in water to form 5 wt %-25 wt % polymer solutions. A tube-inverting test was performed. Specifically, sample flasks containing the solutions of the star-shaped multi-arm polymer were immersed in a 24-80° C. water bath and, after 15 min of equilibration, immediately inverted. If a sample did not noticeably flow within 30 s, then the sample was deemed to be in a gel state, and the temperature at that moment was the solution-gel transition temperature.

In FIG. 3, the triangles indicate temperatures at which precipitation occurs in polymer gels of certain concentrations, and the *rhombi* indicate temperatures at which polymer solutions of certain concentrations transition into gels.

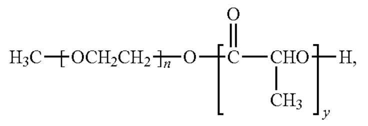

where n is 12, and y is 9.

Figure 4:
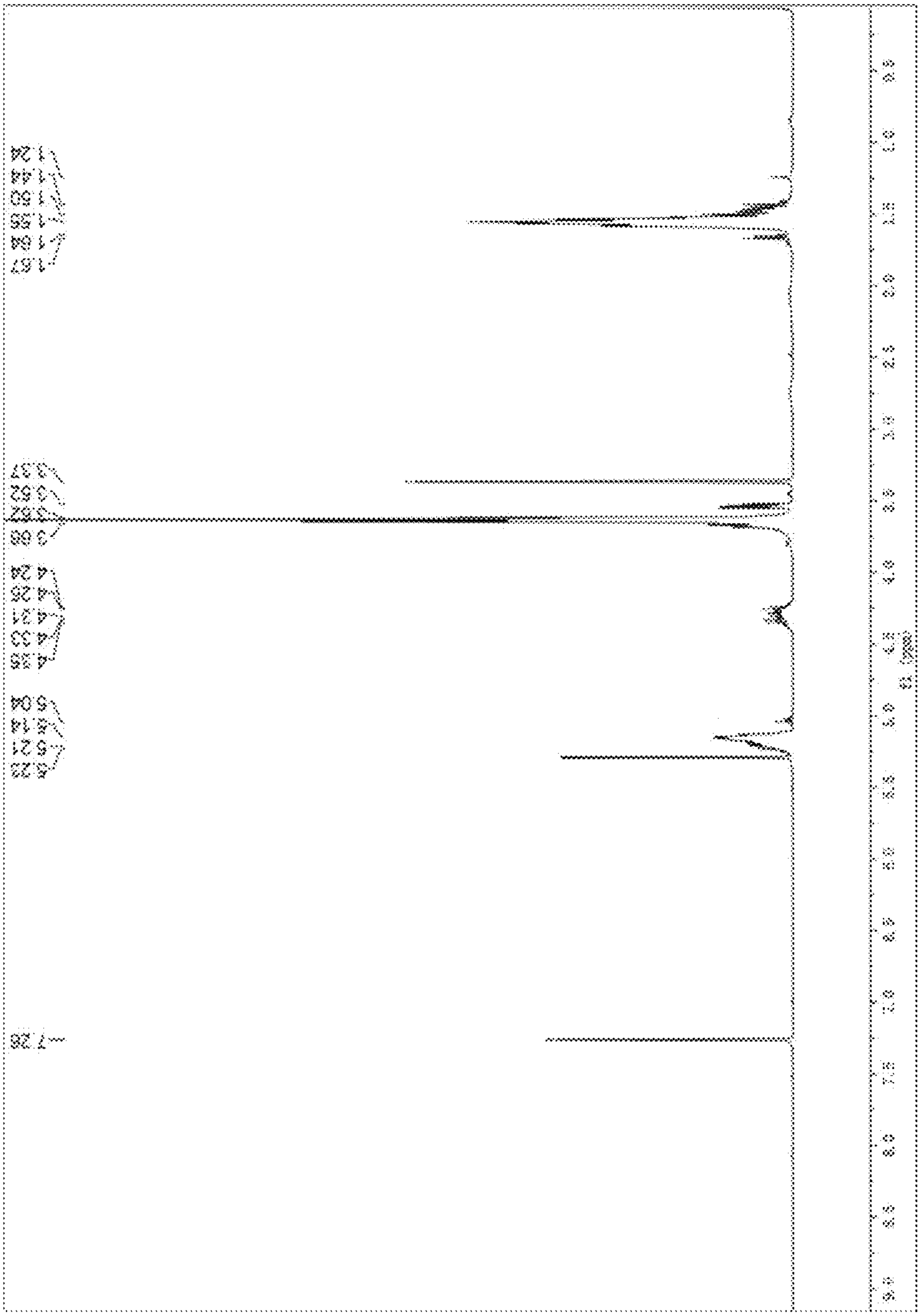
FIG. 4 shows a $^1$H-NMR spectrum of a diblock polymer mPEG-PLA.

FIG. 4 shows a $^{1}$H-NMR spectrum of the polymer mPEG-PLA, where the hydrogen at 3.65 ppm is from the methylene in mPEG, the hydrogen at 3.38 ppm is from the methyl in mPEG, and the hydrogen at 5.1 ppm is from the methine in D,L-lactide. According to areas calculated by integration, the results agree with the ratio of the starting materials.

2.2. Synthesis of Star-Shaped Multi-Arm Polymer PMDA-mPEG-PLA 23 g of the diblock copolymer mPEG-PLA was added to a 100 mL round-bottom flask and dissolved in 160 mL of dichloromethane, and then 1.04 g of pyromellitic dianhydride, 14.46 g of N,N-diisopropylcarbodiimide and 1.40 g of 4-dimethylaminopyridine were sequentially added. The mixture was left to react in a 25° C. oil bath for 24 h. Then a polymer was precipitated using absolute ethanol. The polymer was dried in vacuo to give the final product, namely the star-shaped multi-arm polymer PMDA-mPEG-PLA. Gel permeation chromatography (GPC, polyethylene glycol as standard) analysis showed that the above polymer has a number-average molecular weight (Mn) of 4110 and a weight-average molecular weight (Mw) of 4518, and therefore a molecular weight distribution coefficient (Mw/Mn) of 1.10. The structure of the star-shaped multi-arm polymer PMDA-mPEG-PLA is:

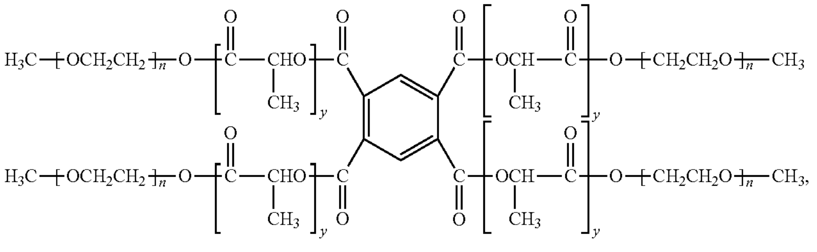

Example 2

2.1. Synthesis of Amphiphilic Diblock Copolymer mPEG-PLA 10 g of mPEG 550 was weighed out and added to a 100 mL round-bottom flask, and dehydrated under vacuum for 1 h with stirring at 130° C. After the temperature was reduced to room temperature, 13 g of D,L-lactide was added, and a solution of stannous octoate (18 mg) in dimethylbenzene was added. Dimethylbenzene was removed by 2 h of vacuumization. The mixture was left to react in a 140° C. oil bath in a nitrogen atmosphere for 16 h. Then the reaction mixture was dissolved in dichloromethane, and a polymer was precipitated using petroleum ether. The polymer was dried in vacuo to give the final product, namely the diblock polymer mPEG-PLA. The block polymer was characterized by gel permeation chromatography (GPC, polyethylene glycol as standard) and found to have a number-average molecular weight (Mn) of 1172 and a weight-average molecular weight (Mw) of 1355, and therefore a molecular weight distribution coefficient (Mw/Mn) of 1.16. The structure of the diblock polymer mPEG-PLA is:

where n is 12, and y is 10.

Figure 5:
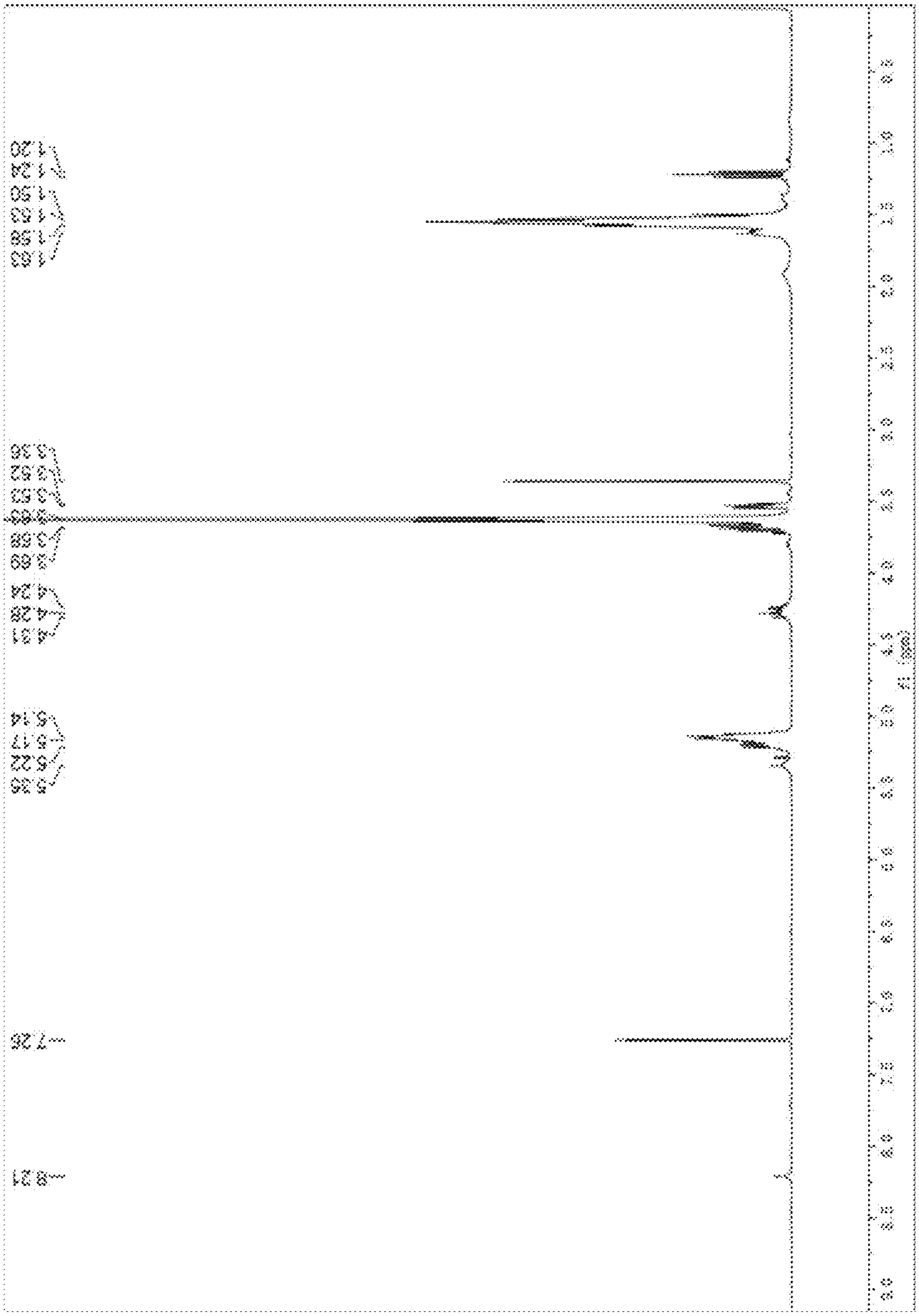
FIG. 5 shows a $^1$H-NMR spectrum of a star-shaped multi-arm polymer PMDA-mPEG-PLA.

FIG. 5 shows a 1H-NMR spectrum of the star-shaped multi-arm polymer PMDA-mPEG-PLA, where in addition to the hydrogens of the diblock polymer described above, a new peak can be seen at 8.2 ppm. The peak belongs to the hydrogen on the benzene ring in PMDA, suggesting that the star-shaped polymer PMDA-mPEG-PLA has been successfully synthesized.

A proper amount of the star-shaped polymer PMDA-mPEG-PLA was mixed with flurbiprofen to form a solution containing 1.59 mg of flurbiprofen and 25% polymer. 1 mL of the flurbiprofen solution was added to a 10 mL test tube, and the test tube was left in a 37° C. water bath for 5 min. After gel formation, 3 mL of PBS pre-heated to 37° C. was added. The test tube was shaken at 37° C. at 50 rpm. After a period of time, 1.5 mL of the supernatant was collected, and an equal amount of PBS pre-heated to 37° C. was added. The drug concentration was determined by HPLC, and the release rate was calculated.

Figure 6:
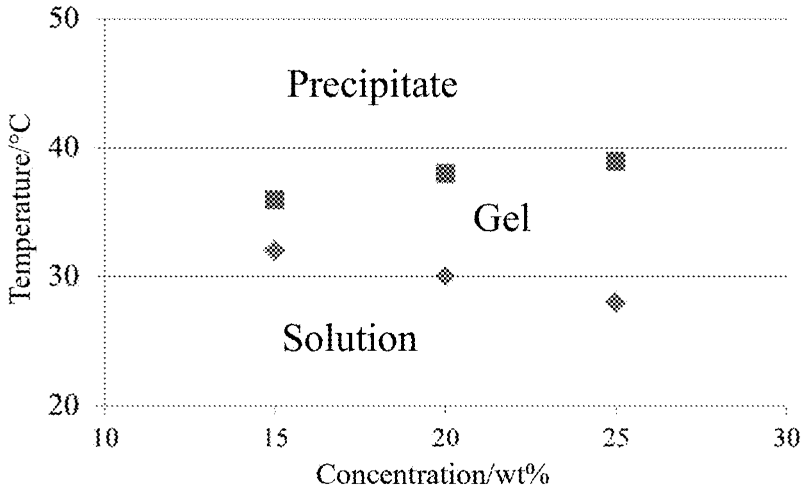
FIG. 6 shows a phase diagram of the solution-gel transition of the star-shaped multi-arm polymer PMDA-mPEG-PLA, where the squares indicate temperatures at which precipitation occurs in polymer gels of certain concentrations, and the *rhombi* indicate temperatures at which polymer solutions of certain concentrations transition into gels.

FIG. 6 shows a phase diagram of the solution-gel transition of the star-shaped multi-arm polymer PMDA-mPEG- PLA. A proper amount of the star-shaped multi-arm polymer was weighed out and dissolved in water to form 10 wt %-25 wt % polymer solutions. A tube-inverting test was performed. Specifically, sample flasks containing the solutions of the star-shaped multi-arm polymer were immersed in a 24-80° C. water bath and, after 15 min of equilibration, immediately inverted. If a sample did not noticeably flow within 30 s, then the sample was deemed to be in a gel state, and the temperature at that moment was the solution-gel transition temperature.

In FIG. 6, the squares indicate temperatures at which precipitation occurs in polymer gels of certain concentrations, and the *rhombi* indicate temperatures at which polymer solutions of certain concentrations transition into gels.

Figure 7:
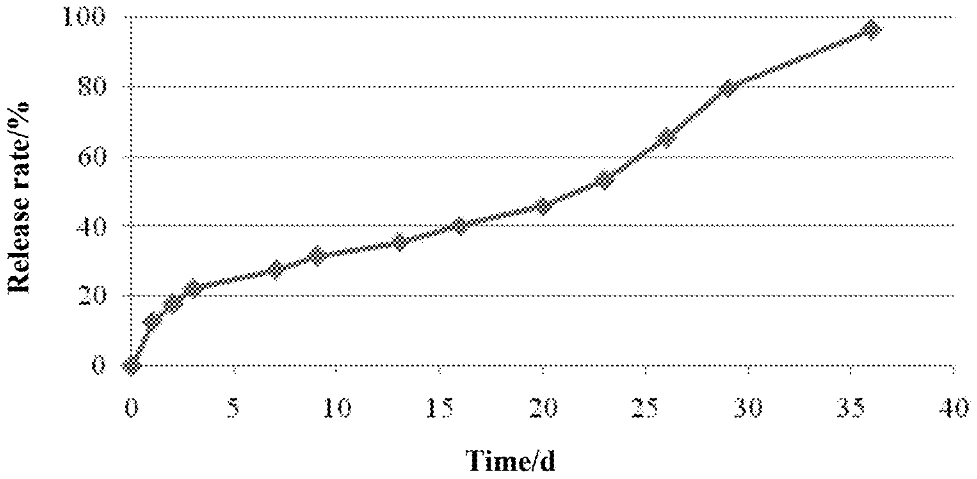
FIG. 7 shows a release curve of a PMDA-mPEG-PLA flurbiprofen hydrogel.

FIG. 7 shows a release curve of the PMDA-mPEG-PLA flurbiprofen hydrogel, where the release rate gradually increases over time, and the final release rate is 96.6%.

1.2. Synthesis of Non-Aromatic Core Star-Shaped Polymer 4-Arm PLGA

To a 100 mL single-necked flask were added 0.8 g of pentaerythritol, 4.7 g of glycolide and 17.78 g of D,L-lactide, followed by a solution of stannous octoate (33 mg) in dimethylbenzene. After 3 h of vacuumization, the mixture was left to react in a 150° C. oil bath in a nitrogen atmosphere for 6 h. After the reaction was complete, the reaction mixture was dissolved in dichloromethane, and a polymer was precipitated using absolute ethanol. The polymer was dried in vacuo to give the final product, namely 4-arm PLGA. Gel permeation chromatography (GPC, polyethylene glycol as standard) analysis showed that the above polymer has a number-average molecular weight (Mn) of 3119 and a weight-average molecular weight (Mw) of 3706, and therefore a molecular weight distribution coefficient (Mw/Mn) of 1.19.

The structure of the non-aromatic core star-shaped polymer 4-arm PLGA is:

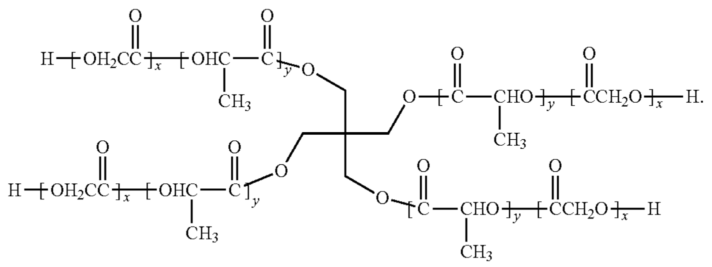

Comparative Example 1

1.1. Synthesis of CMPEG

To a 250 mL round-bottom three-necked flask were added 20 g of purified mPEG 550, 4.37 g of succinic anhydride, 4.45 g of 4-dimethylaminopyridine and 3.68 g of triethylamine, followed by 73 mL of dry 1,4-dioxane. The mixture was left to react at room temperature in a nitrogen atmosphere for 48 h. After the reaction was complete, dioxane was removed under reduced pressure, and dichloromethane was added to dissolve the product. The product was precipitated from petroleum ether and dried in vacuo at 50° C. to give CMPEG.

The structure of CMPEG is:

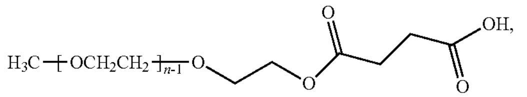

where n−1 is: 11.

Figure 8:
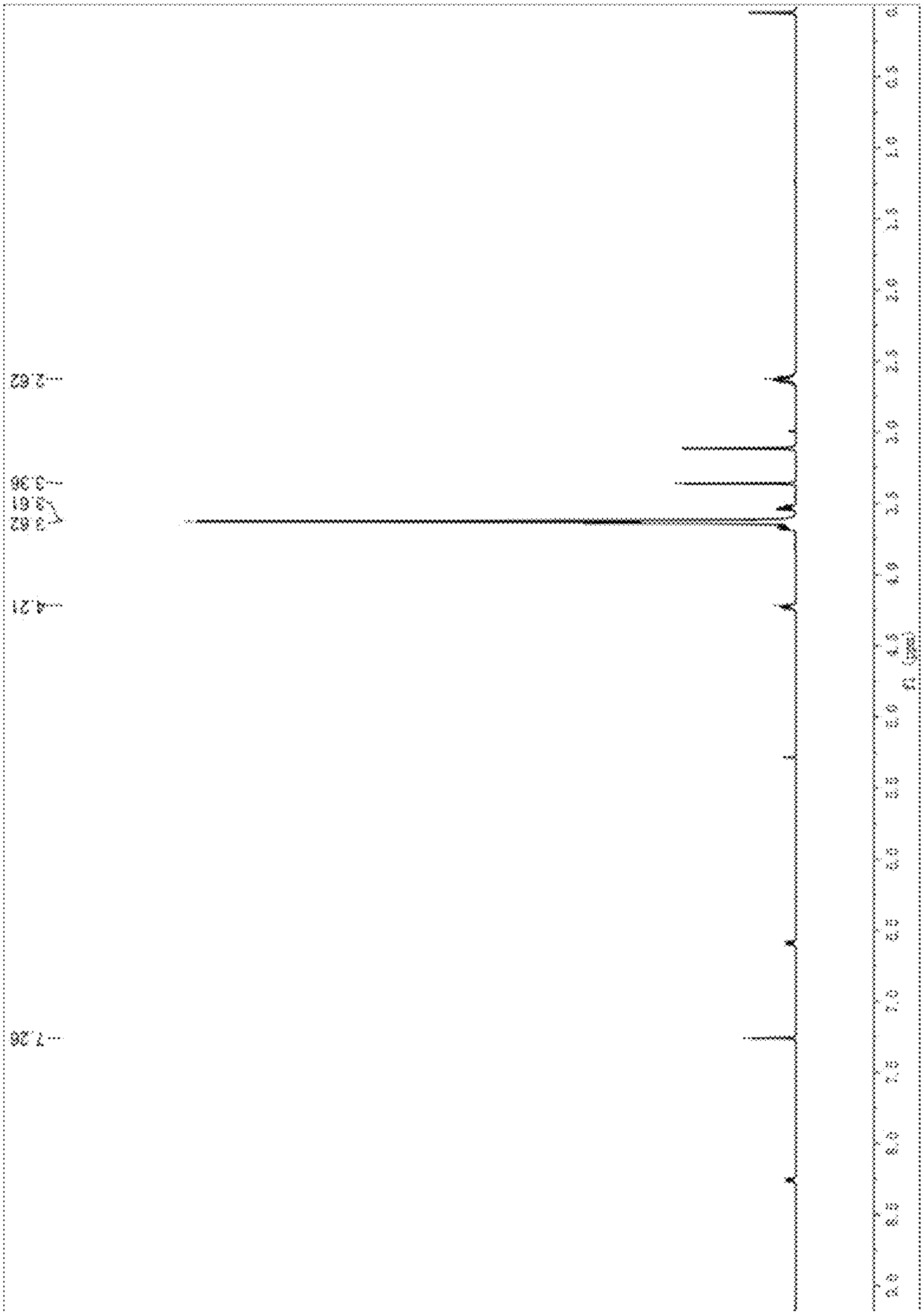
FIG. 8 shows a $^1$H-NMR spectrum of CMPEG.

The product was characterized. FIG. 8 shows a $^{1}$H-NMR spectrum of CMPEG, where n−1 is: 11. The hydrogen at 3.62 ppm is from the methylene in mPEG, the hydrogen at 3.36 ppm is from the methyl in mPEG, and the hydrogen at 2.62 ppm is from the methylene in succinic anhydride.

Figure 9:
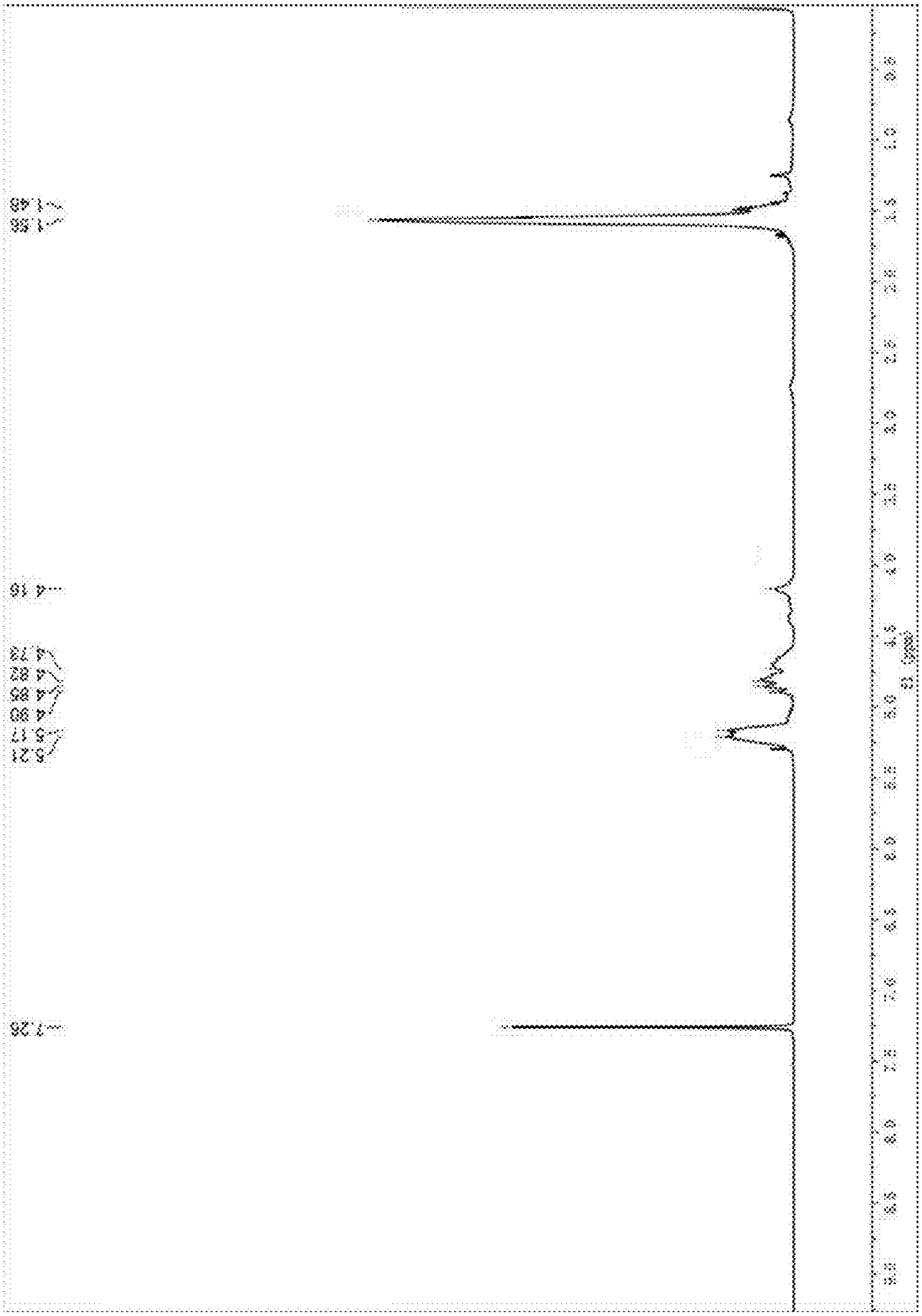
FIG. 9 shows a $^1$H-NMR spectrum of a non-aromatic core star-shaped polymer 4-arm PLGA.

FIG. 9 shows a 1H-NMR spectrum of the non-aromatic core polymer 4-arm PLGA, where the hydrogen at 1.5 ppm is from the methyl in D,L-lactide, the hydrogen at 4.8 ppm is from the methylene in glycolide, the hydrogen at 4.16 ppm is from the methylene on pentaerythritol and the methine and methylene attached to —OH, and the hydrogen at 5.1 ppm is from the methine in D,L-lactide.

1.3. Synthesis of Non-Aromatic Core Star-Shaped Polymer 4-Arm PLGA-PEG

To a 250 mL round-bottom three-necked flask were added 5 g of 4-arm PLGA, 4.19 g of CMPEG, 1.33 g of dicyclohexylcarbodiimide, 0.391 g of 4-dimethylaminopyridine and 80 mL of dry DCM. The mixture was left to react at room temperature in a nitrogen atmosphere for 48 h. After the reaction was complete, the reaction mixture was filtered, and a precipitate was obtained from the filtrate in absolute ethanol. The precipitate was dried in vacuo to give the final product, namely 4-arm PLGA-PEG. Gel permeation chromatography (GPC, polyethylene glycol as standard) analysis showed that the above polymer has a number-average molecular weight (Mn) of 5502 and a weight-average molecular weight (Mw) of 7319, and therefore a molecular weight distribution coefficient (Mw/Mn) of 1.33.

The structure of 4-arm PLGA-PEG is:

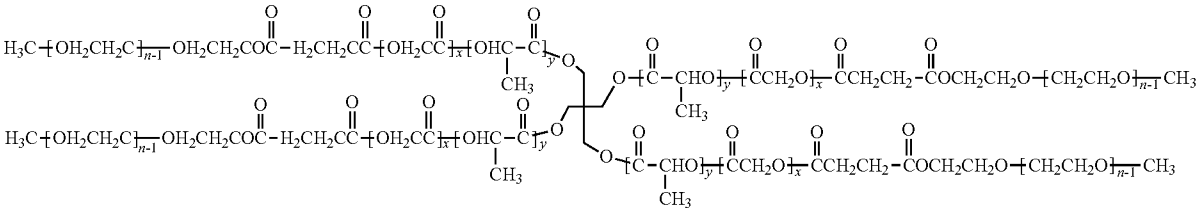

Figure 10:
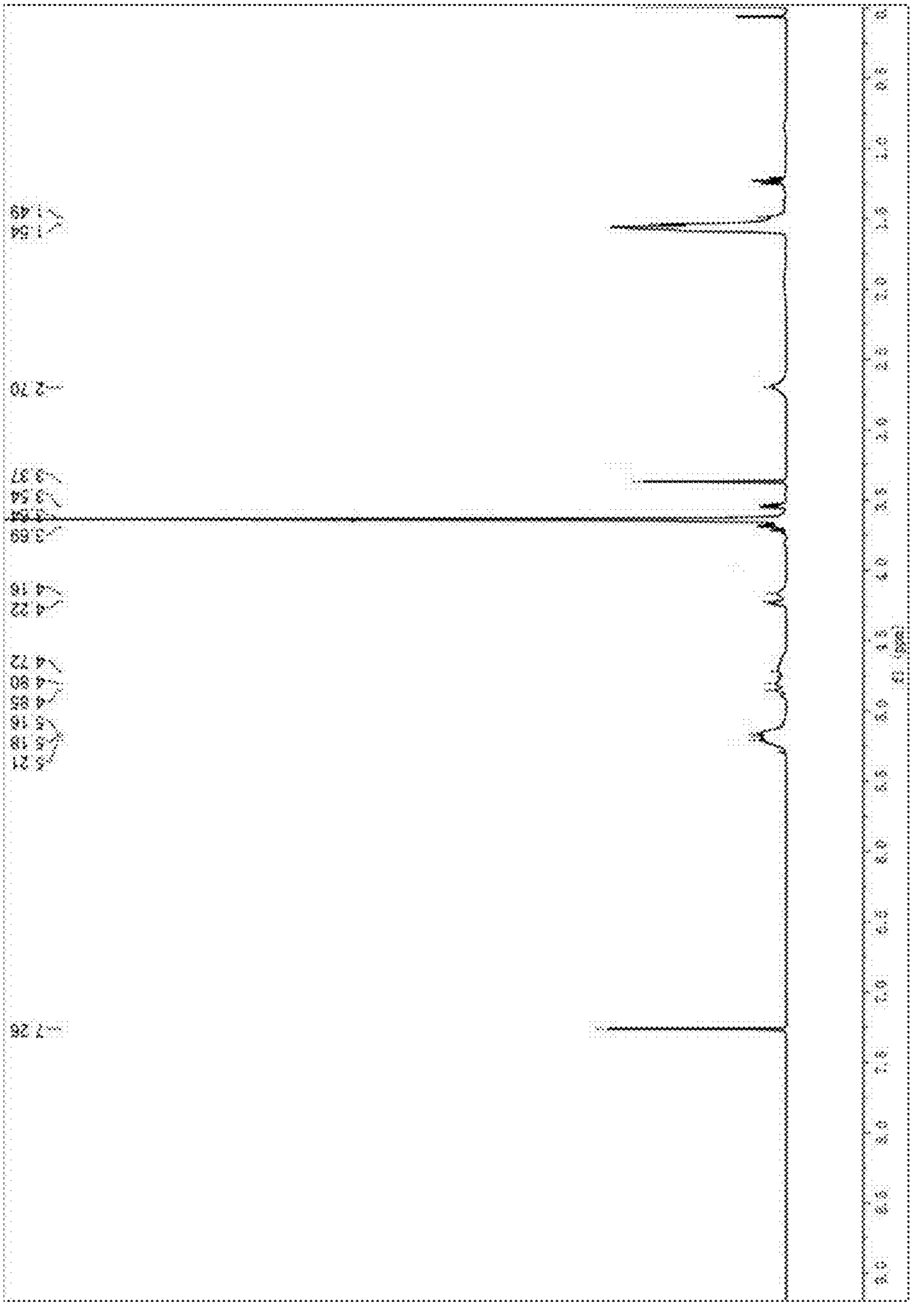
FIG. 10 shows a $^1H$-NMR spectrum of a non-aromatic core star-shaped polymer 4-arm PLGA-PEG.

FIG. 10 shows a 1H-NMR spectrum of the non-aromatic core star-shaped polymer 4-arm PLGA-PEG, where all the hydrogens of CMPEG and 4-arm PLGA-PEG can be found. According to calculations, n−1 is 11, x is 5, and y is 15.

Figure 11:
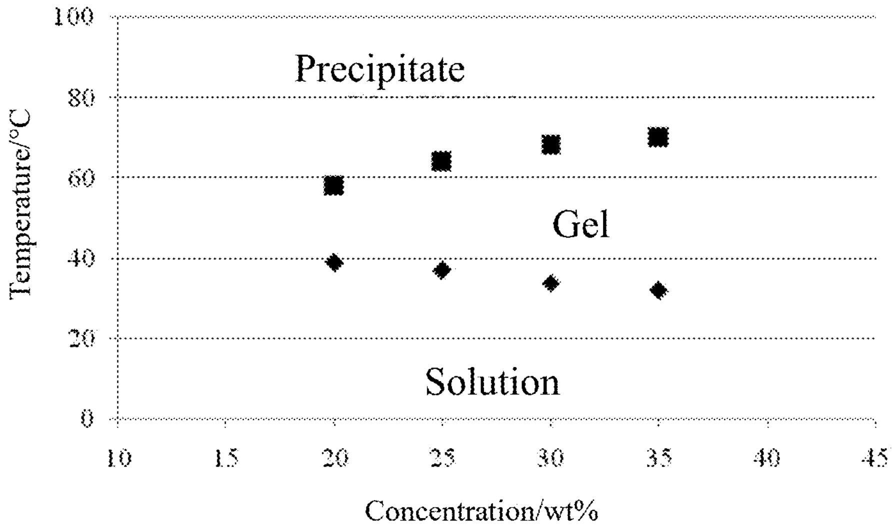
FIG. 11 shows a phase diagram of the solution-gel transition of the non-aromatic core star-shaped polymer 4-arm PLGA-PEG, where the squares indicate temperatures at which precipitation occurs in polymer gels of certain concentrations, and the *rhombi* indicate temperatures at which polymer solutions of certain concentrations transition into gels.

FIG. 11 shows a phase diagram of the solution-gel transition of the non-aromatic core star-shaped polymer 4-arm PLGA-PEG. A proper amount of the star-shaped polymer was weighed out and dissolved in water to form 10 wt %-35 wt % polymer solutions. A tube-inverting test was performed. Specifically, sample flasks containing the solutions of the star-shaped polymer were immersed in a 25-74° C. water bath and, after 15 min of equilibration, immediately inverted. If a sample did not noticeably flow within 30 s, then the sample was deemed to be in a gel state, and the temperature at that moment was the solution-gel transition temperature.

In FIG. 11, the squares indicate temperatures at which precipitation occurs in polymer gels of certain concentrations, and the *rhombi* indicate temperatures at which polymer solutions of certain concentrations transition into gels.

Comparison of FIG. 3 and FIG. 11 shows that the critical gel concentration of PMDA-mPEG-PLGA is 10 wt %, while that of 4-arm PLGA-PEG is 20 wt %.

A proper amount of the non-aromatic core star-shaped polymer 4-arm PLGA-PEG was mixed with flurbiprofen to form a solution containing 1.57 mg of flurbiprofen and 25% polymer. 1 mL of the flurbiprofen solution was added to a 10 mL test tube, and the test tube was left in a 37° C. water bath for 5 min. After gel formation, 3 mL of PBS pre-heated to 37° C. was added. The test tube was shaken at 37° C. at 50 rpm. After a period of time, 1.5 mL of the supernatant was collected, and an equal amount of PBS pre-heated to 37° C. was added. The drug concentration was determined by HPLC, and the release rate was calculated.

Figure 12:
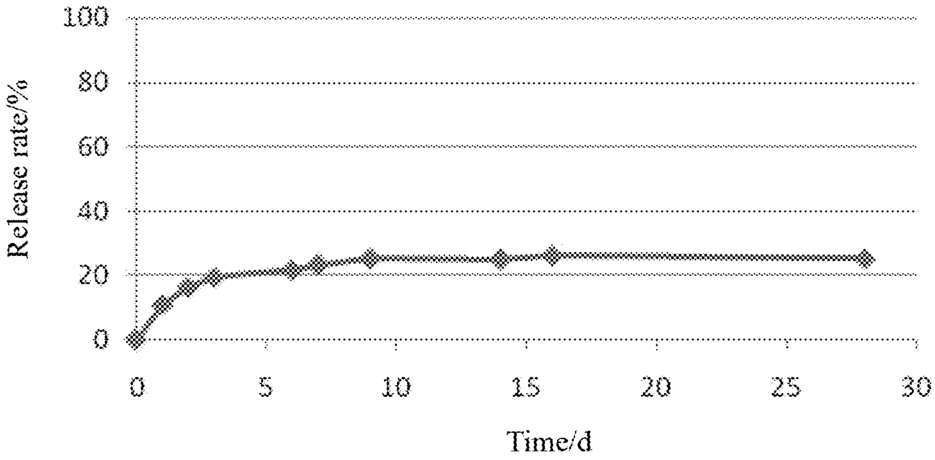
FIG. 12 shows a release curve of a non-aromatic core star-shaped polymer 4-arm PLGA-PEG flurbiprofen hydrogel.

FIG. 12 shows a release curve of the non-aromatic core star-shaped polymer 4-arm PLGA-PEG flurbiprofen hydrogel, where the release rate gradually increases over time, but the final release rate is 26% only.

Comparison with FIG. 6 shows that the PMDA-mPEG-PLA hydrogel exhibited a higher drug release rate than the 4-arm PLGA-PEG hydrogel, and the PMDA-mPEG-PLA hydrogel can more easily encapsulate the drug.

Although the foregoing invention has been described in detail using drawings and examples for a clear understanding, the description and examples should not be construed as limiting the scope of the present disclosure.

The invention claimed is:

1. A thermosensitive polymer having a structure of formula (I-2), (I-2)

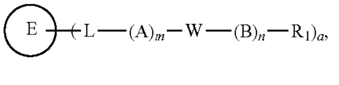

wherein $R_1$ are identical or different and are each independently selected from $C_1$-$C_{12}$ alkyl, and the $C_1$-$C_{12}$ alkyl is optionally substituted with one or more substituents selected from the group consisting of halogen, hydroxy, alkoxy, haloalkoxy, cyano, amino and nitro;

ring E is selected from phenyl;

L are identical or different and are each independently selected from the group consisting of a bond, —C(O)—, —O—, —S—, —SO—, —$SO_2$—, —C(O)O—, —NR'—, —C(O) NR'—, alkylene, alkenylene, alkynylene, heteroalkylene, cycloalkylene, heterocycloalkylene, arylene, heteroarylene and PEG, and the alkylene, alkenylene, alkynylene, heteroalkylene, cycloalkylene, heterocycloalkylene, arylene or heteroarylene is optionally substituted with one or more substituents selected from the group consisting of hydroxy, alkyl, alkoxy, haloalkyl, haloalkoxy, halogen, hydroxy, cyano, amino and nitro;

A are identical or different and are each independently selected from a hydrophobic block, B are identical or different and are each independently selected from a hydrophilic block, wherein the hydrophilic block is selected from the group consisting of polyethylene glycol and polyvinylpyrrolidone, and the hydrophobic block is selected from the group consisting of a polyester and a polyamino acid;

the hydrophobic block is selected from one of poly(DL-lactic acid), poly(D-lactic acid), poly(L-lactic acid), poly(DL-lactic acid-glycolic acid), poly(L-lactic acid-glycolic acid), poly(D-lactic acid-glycolic acid), polycaprolactone, poly(DL-lactic acid-caprolactone), poly (L-lactic acid-caprolactone, poly(D-lactic acid-caprolactone), polyglycine, polyalanine, polyphenylalanine, polyglutamic acid, polylysine, polyornithine and polyarginine or a copolymer thereof;

W are identical or different and are each independently selected from the group consisting of a bond, —O—, —S—, —SO—, —$SO_2$—, —C(O)—, —C(O)O—, —NR'—, —C(O) NR'— and alkylene, and the alkylene is optionally substituted with one or more substituents selected from the group consisting of hydroxy, alkyl, alkoxy, haloalkyl, haloalkoxy, halogen, hydroxy, cyano, amino and nitro;

R' is selected from the group consisting of hydrogen, deuterium, hydroxy, alkyl, alkoxy, cycloalkyl, heterocyclyl, aryl and heteroaryl, and the alkyl, alkoxy, cycloalkyl, heterocyclyl, aryl or heteroaryl is optionally substituted with one or more substituents selected from the group consisting of halogen, hydroxy, oxo, nitro and cyano;

m is selected from an integer from 5-150;

n is selected from an integer from 5-300;

a is selected from an integer from 2-11.

2. The thermosensitive polymer according to claim 1, wherein L are identical or different and are each independently selected from the group consisting of a bond, —C(O)—, —O—, —S—, —SO—, —$SO_2$—, —C(O)O—, —NR'—, —C(O) NR'— and $C_1$-$C_6$ alkylene;

R' is selected from the group consisting of hydrogen, deuterium, hydroxy, $C_1$-$C_6$ alkyl and $C_1$-$C_6$ alkoxy.

3. The thermosensitive polymer according to claim 1, wherein W are identical or different and are each independently selected from the group consisting of a bond, —O—, —C(O)— and —NH—.

4. The thermosensitive polymer according to claim 1, wherein —$(B)_n$—$R_1$ are identical or different and are each independently selected from —$(CH_2CH_2O)_n$—$R_1$, wherein $R_1$ are identical or different and are each independently selected from the group consisting of methyl, ethyl, n-propyl, isopropyl, n-butyl, isobutyl and tert-butyl; n is as defined in claim 1.

5. The thermosensitive polymer according to claim 1, wherein W-$(A)_m$-L is selected from the group consisting of:

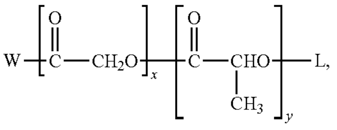

-continued

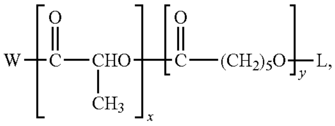

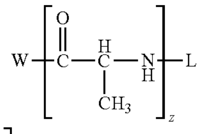

and

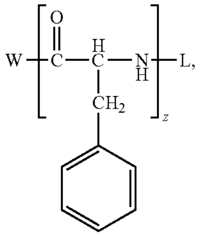

wherein

W and L are as defined in any one of claim 1;

x is selected from an integer from 0-50;

y is selected from an integer from 5-70;

z is selected from an integer from 10-120.

6. The thermosensitive polymer according to claim 5, wherein n is selected from an integer from 5-15;

x is selected from an integer from 3-10;

y is selected from an integer from 5-20; and z is selected from an integer from 15-25.

7. The thermosensitive polymer according to claim 1, being selected from the group consisting of:

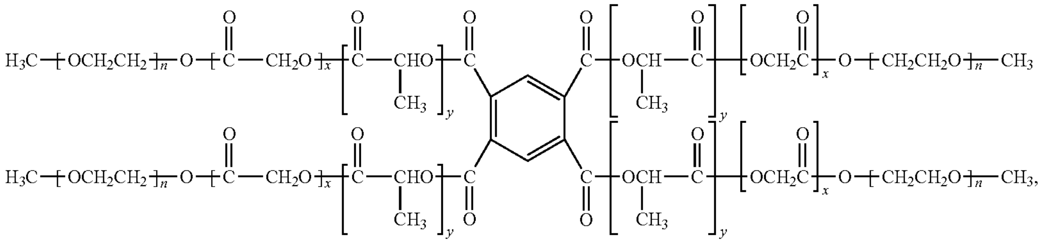

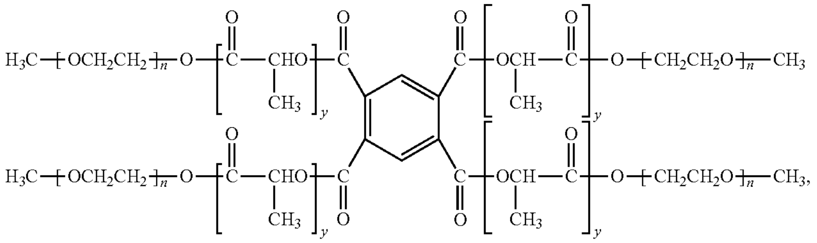

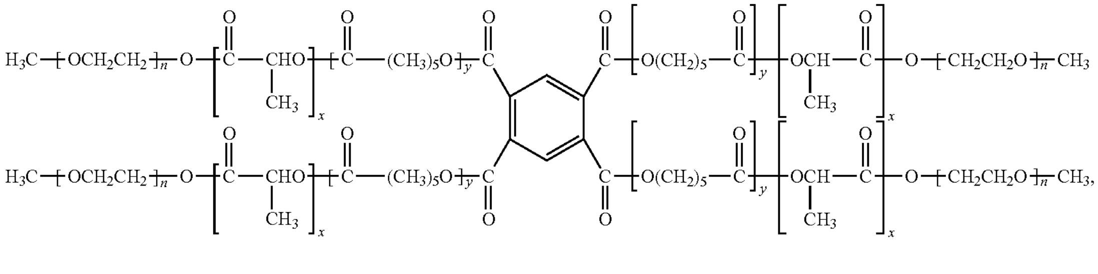

-continued

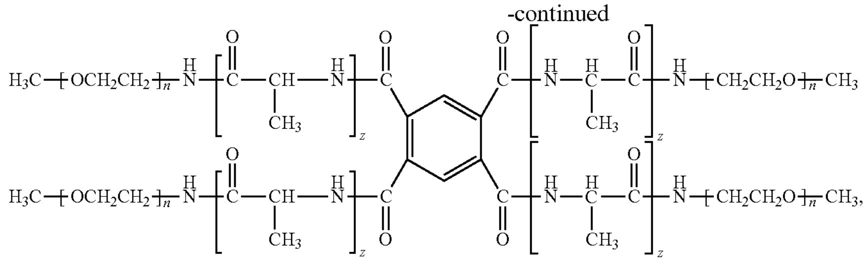

and

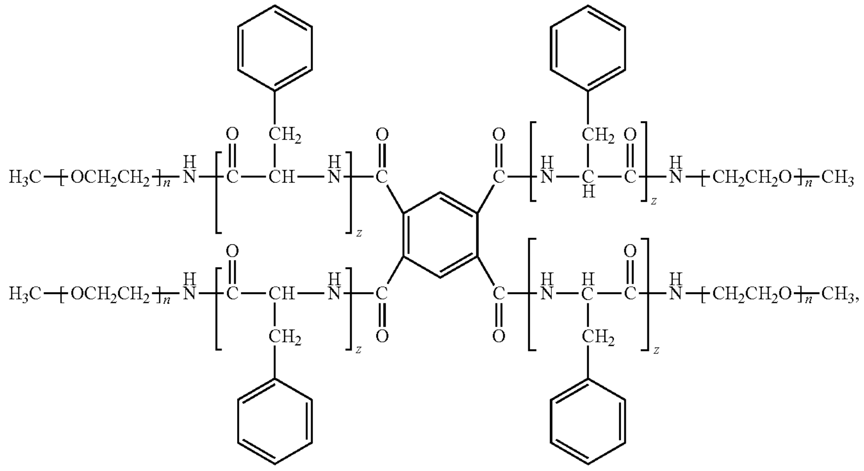

wherein n, x, y and z are as defined in claim 5.

8. The thermosensitive polymer according to claim 1, having a molecular weight distribution coefficient (Mw/Mn) of less than 2.

9. A composition comprising the thermosensitive polymer according to claim 1, wherein the composition further comprises a vehicle.

10. The composition according to claim 9, wherein a concentration of the thermosensitive polymer is 5-50 wt % of total composition.

11. The composition according to claim 9, further comprising a drug or bioactive agent.

12. The composition according to claim 9, being an injectable composition.

13. The thermosensitive polymer according to claim 1, undergoing a solution-gel phase transition as temperature increases, wherein a temperature of the solution-gel phase transition is 20-37° C.

14. The thermosensitive polymer according to claim 1, wherein m is selected from an integer from 10-45;

n is selected from an integer from 10-30; and a is selected from an integer from 3-11.

15. The thermosensitive polymer according to claim 1, wherein m is selected from an integer from 15-25;

n is selected from an integer from 10-20; and a is selected from an integer from 4-8.

16. The thermosensitive polymer according to claim 5, wherein x is selected from an integer from 0-20;

y is selected from an integer from 5-25; and z is selected from an integer from 10-45.

17. A compound, wherein the compound has a structure of formula (I-2) according to any one of claim 1.

18. A method for preparing the thermosensitive polymer according to claim 1, comprising a step of chemically coupling an amphiphilic copolymer comprising a hydrophobic block and a hydrophilic block to an acid anhydride, acyl chloride, active ester or carboxylic acid comprising an aromatic ring or heteroaromatic ring by the action of a condensing agent or catalyst, the condensing agent is selected from one or more of dicyclohexylcarbodiimide, diisopropylcarbodiimide and 1-(3-dimethylaminopropyl)-3-ethylcarbodiimide, and the catalyst is selected from one or more of 4-dimethylaminopyridine, 1-hydroxybenzotriazole and 4-pyrrolidinylpyridine.

19. A hydrogel comprising one or more thermosensitive polymers according to claim 1.

20. A method for enhancing the solubility and/or the stability of a drug or bioactive agent, comprising mixing the drug or bioactive agent into one or more thermosensitive polymers according to claim 1.

21. A method for treating disease, comprising a step of injecting into a physiological environment one or more thermosensitive polymers according to claim 1.

* * * * *